US011844830B2

(12) United States Patent
Weiner et al.

(10) Patent No.: US 11,844,830 B2
(45) Date of Patent: *Dec. 19, 2023

(54) VACCINES FOR HUMAN PAPILLOMA VIRUS AND METHODS FOR USING THE SAME

(71) Applicants: The Trustees of the University of Pennsylvania, Philadelphia, PA (US); Inovio Pharmaceuticals, Inc., Plymouth Meeting, PA (US)

(72) Inventors: David Weiner, Merion, PA (US); Jian Yan, Wallingford, PA (US)

(73) Assignees: The Trustees of the University of Pennsylvania, Philadelphia, PA (US); Inovio Pharmaceuticals, Inc., Plymouth Meeting, PA (US)

(*) Notice: Subject to any disclaimer, the term of this patent is extended or adjusted under 35 U.S.C. 154(b) by 79 days.

This patent is subject to a terminal disclaimer.

(21) Appl. No.: 17/141,704

(22) Filed: Jan. 5, 2021

(65) Prior Publication Data

US 2021/0121560 A1    Apr. 29, 2021

Related U.S. Application Data

(63) Continuation of application No. 16/298,006, filed on Mar. 11, 2019, now Pat. No. 10,905,755, which is a continuation of application No. 15/356,945, filed on Nov. 21, 2016, now Pat. No. 10,226,526, which is a continuation-in-part of application No. 14/774,256, filed as application No. PCT/US2014/025106 on Mar. 12, 2014, now Pat. No. 10,232,030.

(60) Provisional application No. 61/777,198, filed on Mar. 12, 2013.

(51) Int. Cl.
| | |
|---|---|
| A61K 39/12 | (2006.01) |
| C07K 14/025 | (2006.01) |
| C07K 14/005 | (2006.01) |
| A61K 39/145 | (2006.01) |
| C12N 7/00 | (2006.01) |
| A61N 1/32 | (2006.01) |
| A61K 39/00 | (2006.01) |

(52) U.S. Cl.
CPC ............ A61K 39/12 (2013.01); A61K 39/145 (2013.01); A61N 1/327 (2013.01); C07K 14/005 (2013.01); C12N 7/00 (2013.01); A61K 2039/53 (2013.01); A61K 2039/54 (2013.01); A61K 2039/70 (2013.01); C07K 2319/00 (2013.01); C07K 2319/02 (2013.01); C07K 2319/42 (2013.01); C12N 2710/20022 (2013.01); C12N 2710/20034 (2013.01); C12N 2760/16022 (2013.01); C12N 2760/16034 (2013.01); C12N 2760/16041 (2013.01); C12N 2760/16071 (2013.01); C12N 2760/16122 (2013.01); C12N 2760/16134 (2013.01); C12N 2760/16222 (2013.01); C12N 2760/16234 (2013.01); C12N 2800/22 (2013.01)

(58) Field of Classification Search
None
See application file for complete search history.

(56) References Cited

U.S. PATENT DOCUMENTS

| | | |
|---|---|---|
| 4,510,245 A | 4/1985 | Cousens |
| 4,722,848 A | 2/1988 | Paoletti |
| 4,790,987 A | 12/1988 | Compans |
| 4,797,368 A | 1/1989 | Carter |
| 4,920,209 A | 4/1990 | Davis |
| 4,945,050 A | 7/1990 | Sanford |
| 5,017,487 A | 5/1991 | Stunnenberg |
| 5,036,006 A | 7/1991 | Sanford |
| 5,077,044 A | 12/1991 | Stocker |
| 5,110,587 A | 5/1992 | Paoletti |
| 5,112,749 A | 5/1992 | Brey, III |
| 5,174,993 A | 12/1992 | Paoletti |
| 5,223,424 A | 6/1993 | Cochran |
| 5,225,336 A | 7/1993 | Paoletti |
| 5,240,703 A | 8/1993 | Cochran |
| 5,242,829 A | 9/1993 | Panicali |
| 5,294,441 A | 3/1994 | Curtiss, III |
| 5,294,548 A | 3/1994 | McLinden |
| 5,310,668 A | 5/1994 | Ellis |
| 5,387,744 A | 2/1995 | Curtiss, III |
| 5,389,368 A | 2/1995 | Curtiss, III |
| 5,424,065 A | 6/1995 | Curtiss, III |
| 5,451,499 A | 9/1995 | Cochran |
| 5,453,364 A | 9/1995 | Paoletti |
| 5,462,734 A | 10/1995 | Letchworth, III |
| 5,470,734 A | 11/1995 | Sondermeijer |
| 5,474,935 A | 12/1995 | Chatterjee |
| 5,482,713 A | 1/1996 | Paoletti |
| 5,580,859 A | 12/1996 | Felgner |
| 5,591,439 A | 1/1997 | Plotkin |
| 5,593,972 A | 1/1997 | Weiner |
| 5,643,579 A | 7/1997 | Hung |
| 5,650,309 A | 7/1997 | Wong-Staal |

(Continued)

FOREIGN PATENT DOCUMENTS

| | | |
|---|---|---|
| CN | 1163634 | 10/1997 |
| CN | 1381583 | 11/2002 |

(Continued)

OTHER PUBLICATIONS

Yan et al. Induction of Antitumor Immunity In vivo Following Delivery of a Novel HPV-16 DNA Vaccine Encoding an E6/E7 Fusion antigen. Vaccine 27 (2009) 431-440.*

(Continued)

Primary Examiner — Nianxiang Zou
(74) Attorney, Agent, or Firm — Riverside Law LLP

(57) ABSTRACT

Improved anti-HPV immunogens and nucleic acid molecules that encode them are disclosed. Immunogens disclosed include those having consensus HPV39 E6E7 and HPV45 E6E7. Pharmaceutical composition, recombinant vaccines comprising DNA plasmid and live attenuated vaccines are disclosed as well methods of inducing an immune response in an individual against HPV are disclosed.

6 Claims, 8 Drawing Sheets

Specification includes a Sequence Listing.

(56) References Cited

U.S. PATENT DOCUMENTS

| | | | |
|---|---|---|---|
| 5,676,594 | A | 10/1997 | Joosten |
| 5,698,202 | A | 12/1997 | Ertl |
| 5,703,055 | A | 12/1997 | Felgner |
| 5,739,118 | A | 4/1998 | Carrano |
| 5,817,637 | A | 10/1998 | Weiner |
| 5,830,876 | A | 11/1998 | Weiner |
| 5,955,088 | A | 9/1999 | Ghiasi |
| 5,962,428 | A | 10/1999 | Carrano |
| 5,981,505 | A | 11/1999 | Weiner |
| 6,034,298 | A | 3/2000 | Lam |
| 6,042,836 | A | 3/2000 | Berman |
| 6,156,319 | A | 12/2000 | Cohen |
| 6,365,160 | B1 | 4/2002 | Webb |
| 6,589,529 | B1 | 7/2003 | Choi |
| 7,245,963 | B2 | 7/2007 | Draghia-Akli |
| 8,221,970 | B2 | 7/2012 | Chau |
| 2005/0031638 | A1 | 2/2005 | Dalemans |
| 2005/0052630 | A1 | 3/2005 | Smith |
| 2005/0100554 | A1 | 5/2005 | Jackson |
| 2007/0275003 | A1 | 11/2007 | Cassetti |
| 2010/0158930 | A1 | 6/2010 | Zhu |
| 2010/0189730 | A1 | 7/2010 | Weiner |
| 2012/0053509 | A1* | 3/2012 | Weiner ............... A61P 37/04 604/20 |
| 2013/0004529 | A1 | 1/2013 | Weiner |

FOREIGN PATENT DOCUMENTS

| | | |
|---|---|---|
| CN | 1720060 | 1/2006 |
| CN | 101280316 A | 10/2008 |
| CN | 101591646 A | 12/2009 |
| CN | 101679475 | 3/2010 |
| CN | 102002105 | 4/2011 |
| CN | 102228698 | 11/2011 |
| CN | 102286104 | 12/2011 |
| CN | 102292089 | 12/2011 |
| JP | 2002518037 A | 6/2002 |
| JP | 2011506272 A | 3/2011 |
| JP | 2011509659 A | 3/2011 |
| JP | 2011516070 A | 5/2011 |
| WO | 1992005248 | 4/1992 |
| WO | 9416737 A1 | 8/1994 |
| WO | 9705164 A1 | 2/1997 |
| WO | 1999010375 | 3/1999 |
| WO | 1999033488 | 7/1999 |
| WO | 1999033868 | 7/1999 |
| WO | 9967285 | 12/1999 |
| WO | 0114416 A2 | 3/2001 |
| WO | 2001017542 A1 | 3/2001 |
| WO | 200157159 A1 | 8/2001 |
| WO | 2004030636 A2 | 4/2004 |
| WO | 2005033333 A2 | 4/2005 |
| WO | 2005060993 | 7/2005 |
| WO | 2007095320 | 8/2007 |
| WO | 2007119896 | 10/2007 |
| WO | 2007121894 | 11/2007 |
| WO | 2008014521 A2 | 1/2008 |
| WO | 2009073330 A2 | 6/2009 |
| WO | 2009099716 | 8/2009 |
| WO | 2009124312 A2 | 10/2009 |
| WO | 2010001409 | 1/2010 |
| WO | 2010017542 A1 | 2/2010 |
| WO | 2010054482 | 5/2010 |
| WO | 2010057159 A2 | 5/2010 |
| WO | 2010079505 | 7/2010 |
| WO | 2013055326 A2 | 4/2013 |

OTHER PUBLICATIONS

Munoz. Human papillomavirus and cancer: the epidemiological evidence. Journal of Clinical Virology 19 (2000) 1-5.*

Andre, S., et al., Increased immune response elicited by DNA vaccination with a synthetic gp120 sequence with optimized codon usage. J Virol, 1998. 72(2): p. 1497-1503.

Bird et al. The Functional Efficiency of a Mammalian Signal Peptide Is Directly Related to Its Hydrophobicity. JBC, 1990, 265: 8420-8425.

Fioretti et al., "DNA Vaccines: Developing New Strategies against Cancer," J Biomed Biotechnol. 2010;2010:174378.

Frelin, L., et al., 'Codon optimization and mRNA amplification effectively enhances the immunogenicity of the hepatitis C virus nonstructural 3/4A gene.' Gene Ther, 2004, 11(6): 522-533.

GenBank: ABP99832.1 . E6 [Human papillomavirus type 45]. Dated Jan. 15, 2009. 1 page.

GenBank: AFO63373.1. E7 [Human papillomavirus type 45]. Dated Mar. 24, 2013. 1 page.

Goldsborough et al., "Nucleotide Sequence of Human Papillomavirus Type 31: A Cervical Neoplasia-Associated virus", Virology, 171; 306-311, (1989).

Hirao, L et al., 'Combined effects of IL-12 and electroporation enhances the potency of DNA vaccination in macaques', Vaccine, 2008, 26:3112-3120.

Hirao, L.A. et al., 'Intradermal subcutaneous immunization by electroporation improves plasmid vaccines delivery and potency in pigs and rhesus macaques', Vaccine, 2008, 26(3):440-448.

Karanam B et al, "Vaccination with HPV16 L2E6E7 fusion protein in GPI-0100 adjuvant elicits protective humoral and cell-mediated immunity", Vaccine, Elsevier Ltd, GB, vol. 27, No. 7, doi:10.1016/J.VACCINE.2008.11.099, ISSN 0264-410X, (Feb. 11, 2009), pp. 1040-1049, (Dec. 16, 2008), XP026079997.

Laddy Dominick J et al, 'Immunogenicity of novel consensus-based DNA vaccines against avian influenza.', VACCINE Apr. 20, 2007 LNKD—PUBMED:17306909, (Apr. 20, 2007), vol. 25, No. 16, ISSN 0264-410X, pp. 2984-2989, XP022004278.

Luckay A, et al., 'Effect of plasmid DNA vaccine design and in vivo electroporation on the resulting vaccine-specific immune responses in rhesus macaques', J. Virol, 2007, 81(10):5257-69.

Mahdavi et al., "Vaccines Against Human Papillomavirus and Cervical Cancer: Promises and Challenges," The Oncologist, vol. 10, Issue 7, Aug. 2005, pp. 528-538.

Munoz et al. Human papillomavirus and cancer: the epidemiological evidence. Journal of Clinical Virology 19 (2000) 1-5.

Peng et al., "Characterization of Human Papillomavirus Type 11-Specific Immune Responses in a Preclinical Model," Laryngoscope. Mar. 2010 ; 120(3): 504-510.

Rolland et al., 'Reconstruction and function of ancestral center-of-tree human immunodeficiency virus type 1 proteins,' J. Virol., 2007, 81(16):8507-14.

Shin et al., 'Induction of robust cellular immunity against HPV6 and HPV11 in mice by DNA vaccine encoding for E6/E7 antigen', Human Vaccines & Immunotherapeutics, (Feb. 16, 2012), vol. 8, No. 4, pp. 470-478, XP055228058.

Y. Xu et al, "Type-specific and cross-reactive antibodies induced by human papillomavirus 31 L1/L2 virus-like particles", Journal of Medical Microbiology, (Jul. 1, 2007), vol. 56, No. 7, doi: 10.1099/jmm.0.47073-0, ISSN 0022-2615, pp. 907-913, XP055107307.

Yan et al. Cellular immunity induced by a novel HPV18 DNA vaccine encoding an E6/E7 fusion consensus protein in mice and rhesus macaques. Vaccine Sep. 19, 2008, vol. 26, Issue 40, pp. 5210-5215.

Yan, J et al., 'Induction of antitumor immunity in vivo following delivery of a novel HPV-16 DNA vaccine encoding an E6/E7 fusion antigen', Vaccine, Elsevier Ltd, GB LNKD-DOI:10.1016/J. Vaccine, 2009, 27:431-440.

* cited by examiner

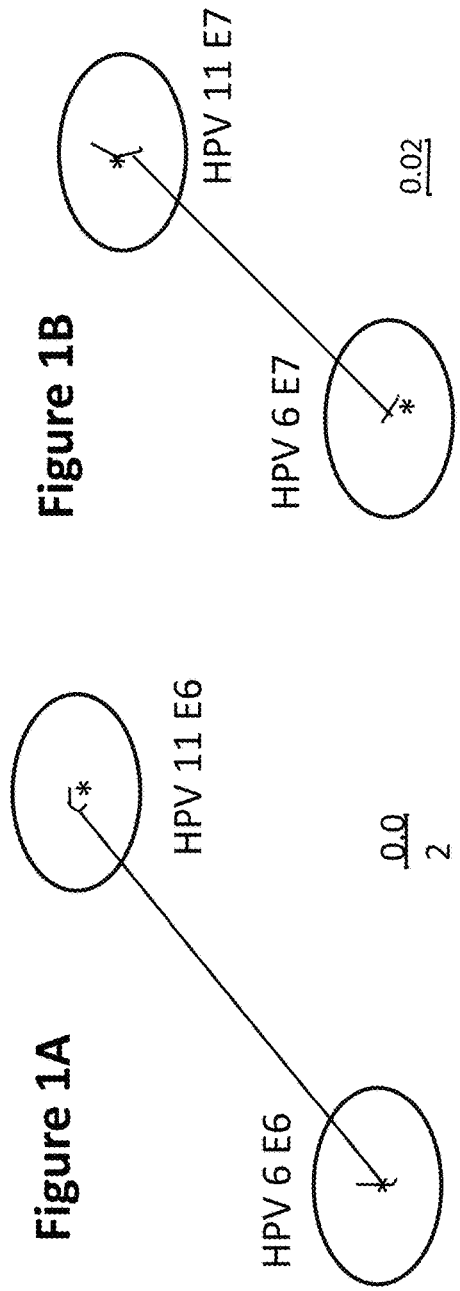
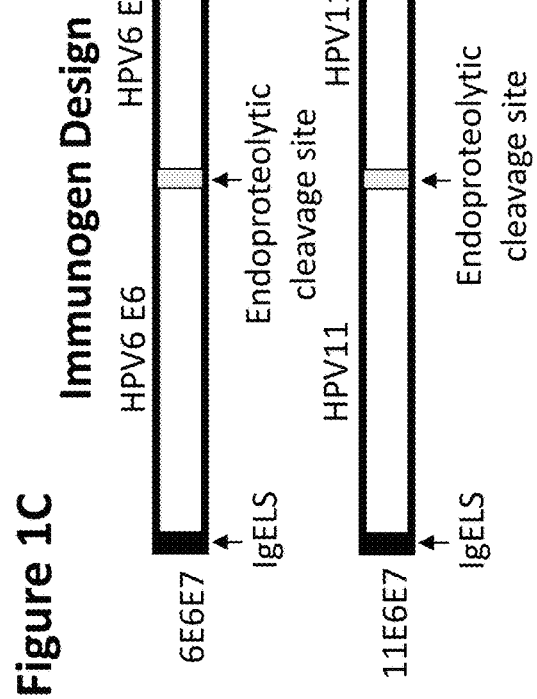
Figure 1A
Figure 1B
Figure 1C
Figure 1A- Figure 1C

Figure 2A
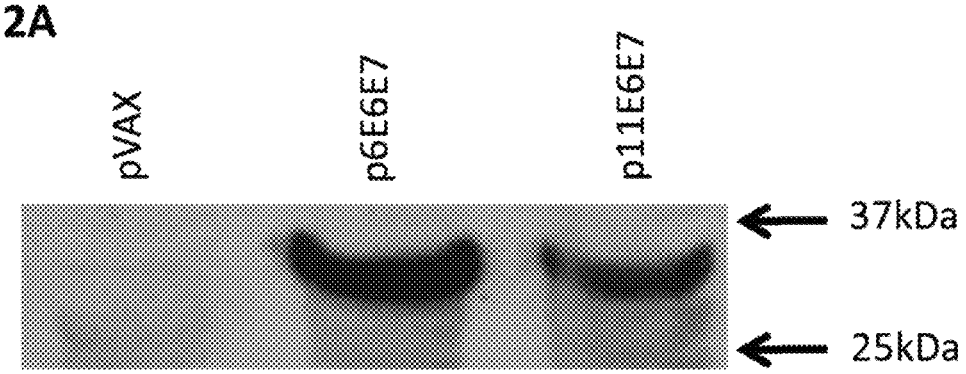
Figure 2B
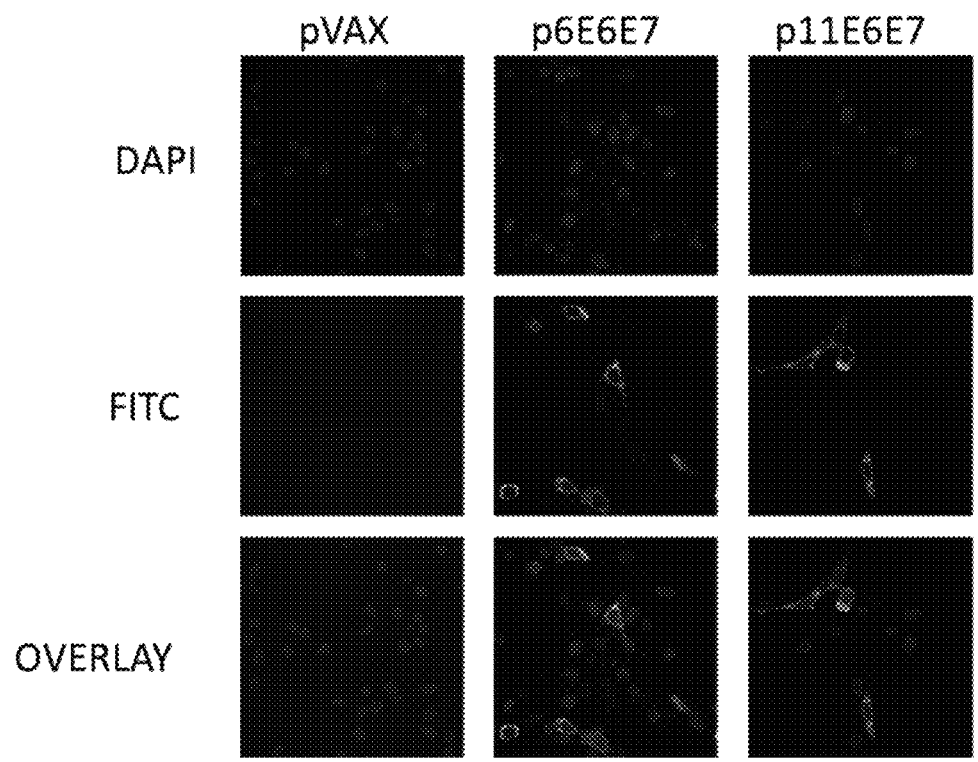
Figure 2A – Figure 2B

Figure 3A
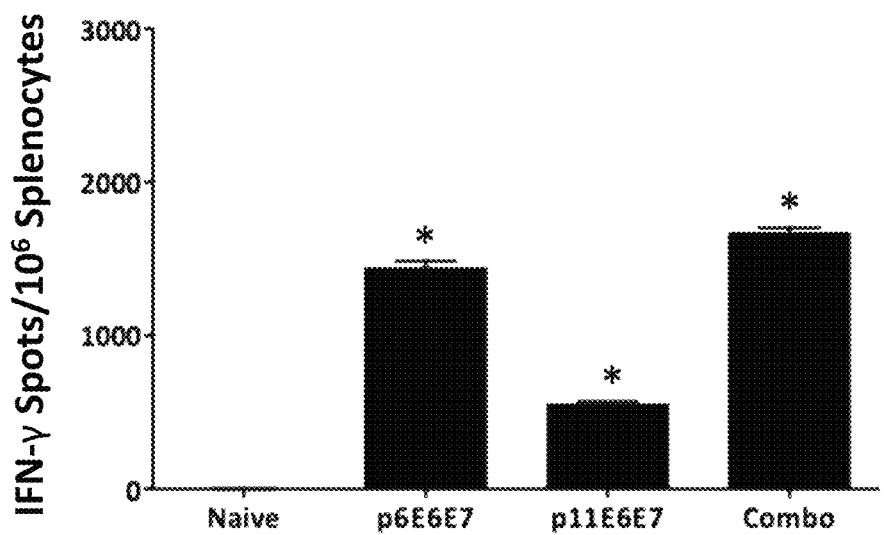
Figure 3B
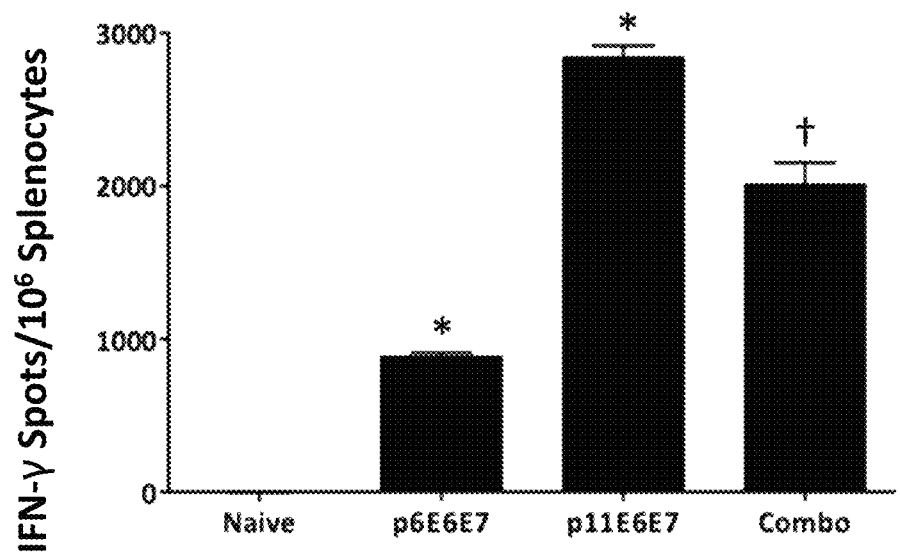
Figure 3A – Figure 3B

```
     E5
      ↑
  1  MDWTWILFLV  AAATRVHSFK  NPAESGRKLH  ELSSALEIPY  DELRLNCVYC  KGQLTETEVL
     ‾‾‾‾‾‾‾‾‾‾‾‾‾‾‾‾‾‾
            IgEL     **

61  DTDLTIVYRD  DTPYGVCTKC  LRFYSKVSEF  RWYRYSVYGT  TLEKLTNKGI  CDLLIRCITC
                     ▲
                                                                          E7
                                                                           ↑
121  QRPLQRHLDK  KKRFHNIGGR  WTGRCIVCWR  RPRTETQVRG  RKRRS RGETP  TLQDYVLDLQ
                     ◀                              ░░░░░░░

181  PEATDLHGYG  QLPDSSDEED  VIDSPAGQAK  PDTSNYNIVT  FCCQCESTLR  LCVQSTQVDI
                     **
                     **

241  RILQELLMGS  FGIVCPMCST  RL
```

Figure 6

```
  1 MDWTWILFLV AAATRVHSFE DPATSGRTLH ELCEVLEESV HEIRLQCVQC KKELQRREVY
          IgEL                        **

61 KTDLRIVYRD NNPYGVCIMC LRFLSKISEY RHYQYSLYGK TLEERVRKPL SEITIRCIIC

121 QTPLERHVNA NKRFHNIMGR WTGRCSECWR PRPVTQVRGR KRRSRGDKAT IKDYILDLQP

181 ETTDLHGYGQ LGDSSDEEDT DGVDRPDGQA EQATSNYYIV TYCHSCDSTL RLCIHSTATD
         **

241 LRTLQQMLLG TLQVVCPGCA RL
```

Figure 7

VACCINES FOR HUMAN PAPILLOMA VIRUS AND METHODS FOR USING THE SAME

CROSS-REFERENCE TO RELATED APPLICATIONS

This application is a continuation of U.S. application Ser. No. 16/298,006, filed Mar. 11, 2019, which is a continuation of U.S. application Ser. No. 15/356,945 filed on Nov. 21, 2016, which is a continuation-in-part of U.S. application Ser. No. 14/774,256, filed Sep. 10, 2015, which is the U.S. national stage application filed under 35 U.S.C. § 371 claiming benefit to International Patent Application No. PCT/US14/025106, filed Mar. 12, 2014, which is entitled to priority under 35 U.S.C. § 119(e) to U.S. Provisional Application No. 61/777,198, filed Mar. 12, 2013, the disclosures of which are incorporated herein by reference in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "206108-0009-32US_Sequence_Listing.txt"; created on Dec. 31, 2020, and 36,743 bytes in size, is hereby incorporated by reference.

FIELD OF THE INVENTION

The present invention relates to improved human papillomavirus (HPV) vaccines, improved methods for inducing immune responses, and for prophylactically and/or therapeutically immunizing individuals against HPV.

BACKGROUND OF THE INVENTION

Papillomavirus are small DNA viruses that comprise up to seven early genes and two late genes. Generally, papilloma virus early genes are designated E1-E7, and papilloma virus late genes are designated L1 and L2. Several species of animals can be infected by members of the papillomavirus family.

Human Papillomavirus (HPV) infection is common and can be transmitted sexually. HPV have been differentiated into 56 or more types based upon DNA sequence homology. HPV types 16 and 18, which cause epithelial dysplasia and other lesions, are often associated with an increased risk of cancer, particularly in situ and invasive carcinomas of the cervix, vagina, vulva and anal canal. Nearly 88% of cervical cancers worldwide are the result of HPV subtypes 16, 18, 45, 31, 33, 52 and 58. Furthermore, various studies have revealed the presence of HPV6 and HPV11 in most incidences of recurrent respiratory papillomatosis. Though known for their association with genital warts and only found in a small percentage of cervical cancer cases, HPV6 and HPV11 have been found in 2.6-5.2% of all cases of low-grade cervical lesions. Furthermore, HPV6 and HPV11 have now been associated with approximately 20% of low-grade squamous intraepithelial lesions that are now considered precursors to cervical cancer, including grade 2 and 3 cervical intraepithelial neoplasia and mild cervical dysplasia. Increasing studies have revealed the association of the two serotypes with various forms of otolaryngologic diseases, including genital warts, recurrent respiratory papillomatosis, lung carcinoma, tonsillar carcinoma, laryngeal carcinoma, and other malignant transformations of otherwise benign neoplasms and dysplasia of the head and neck. The findings of this study shed light and future promise in the use of consensus sequence DNA vaccines against HPV6 and HPV11.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platforms immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens may be able to increase the breadth of the cellular immune response as compared to native antigens alone [Yan., J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

There remains a need for improved vaccines and methods for preventing and treating HPV infection, in particular infections leading to cervical cancer and/or carcinomas of the lung, tonsil, and larynx.

SUMMARY OF THE INVENTION

Aspects of the invention provide compositions comprising at least one nucleotide sequence comprising an HPV E6-E7 fusion antigen selected from the group consisting of: HPV6, HPV11, HPV16, HPV18, HPV31, HPV33, HPV39, HPV45, HPV52, and HPV58.

Another aspect provides compositions comprising one or more nucleotide sequences encoding an HPV E6-E7 fusion antigen selected from the group consisting of: nucleotide sequence that encodes SEQ ID NO:2; nucleotide sequence that encodes SEQ ID NO:4; nucleotide sequence that encodes SEQ ID NO:6; nucleotide sequence that encodes SEQ ID NO:8; nucleotide sequence that encodes SEQ ID NO:18; nucleotide sequence that encodes SEQ ID NO:20; nucleotide sequence that encodes SEQ ID NO:22; nucleotide sequence that encodes SEQ ID NO:24; nucleotide sequence that encodes SEQ ID NO:25; nucleotide sequence that encodes SEQ ID NO:26; a nucleic acid sequence that is at least 95% homologous to a nucleic acid sequence nucleotide sequence that encodes SEQ ID NO:2; a nucleic acid sequence that is at least 95% homologous to a nucleotide sequence that encodes SEQ ID NO:4; a nucleic acid sequence that is at least 95% homologous to a nucleotide sequence that encodes SEQ ID NO:6; a nucleic acid sequence that is at least 95% homologous to a nucleotide sequence that encodes SEQ ID NO:8; a nucleic acid sequence that is at least 95% homologous to a nucleotide sequence that encodes SEQ ID NO:18; a nucleic acid sequence that is at least 95% homologous to a nucleotide sequence that encodes SEQ ID NO:20; a nucleic acid sequence that is at least 95% homologous to a nucleotide sequence that encodes SEQ ID NO:22; a nucleic acid sequence that is at least 95% homologous to a nucleotide sequence that encodes SEQ ID NO:24; a nucleic acid sequence that is at least 95% homologous to a nucleotide sequence that encodes SEQ ID NO:25; a nucleic acid sequence that is at least 95% homologous to a nucleotide sequence that encodes SEQ ID NO:26; a fragment of a nucleotide sequence that encodes SEQ ID NO:2; a fragment of a nucleotide sequence that encodes SEQ ID NO:4; a fragment of a nucleotide sequence that encodes SEQ ID NO:6; a fragment of a nucleotide sequence that encodes SEQ ID NO:8; a fragment of a nucleotide sequence that encodes SEQ ID NO:18; a fragment of a nucleotide sequence that encodes SEQ ID NO:20; a fragment of a nucleotide sequence that encodes SEQ ID NO:22; a fragment of a nucleotide sequence that encodes SEQ ID NO:24; a fragment of a nucleotide sequence that encodes SEQ ID NO:25; a fragment of a nucleotide sequence that encodes SEQ ID NO:26; a nucleic acid sequence that is at least 95% homologous to a fragment of a nucleotide sequence that encodes SEQ ID NO:2; a nucleic acid sequence that is at least 95% homologous to a fragment of a nucleotide sequence that encodes SEQ ID NO:4; a nucleic acid sequence that is at least 95% homologous to a fragment of a nucleotide sequence that encodes SEQ ID NO:6; a nucleic acid sequence that is at least 95% homologous to a fragment of a nucleotide sequence that encodes SEQ ID NO:8; a nucleic acid sequence that is at least 95% homologous to a fragment of a nucleotide sequence that encodes SEQ ID NO:18; a nucleic acid sequence that is at least 95% homologous to a fragment of a nucleotide sequence that encodes SEQ ID NO:20; a nucleic acid sequence that is at least 95% homologous to a fragment of a nucleotide sequence that encodes SEQ ID NO:22; a nucleic acid sequence that is at least 95% homologous to a fragment of a nucleotide sequence that encodes SEQ ID NO:24; a nucleic acid sequence that is at least 95% homologous to a fragment of a nucleotide sequence that encodes SEQ ID NO:25; and a nucleic acid sequence that is at least 95% homologous to a fragment of a nucleotide sequence that encodes SEQ ID NO:26. In some embodiments, The the nucleotide sequences encoding the HPV E6-E7 fusion antigen are without a leader sequence at 5' end that is a nucleotide sequence that encodes SEQ ID NO:10.

In another aspect of the invention, there are provided compositions comprising one or more nucleotide sequences encoding an HPV E6-E7 fusion antigen selected from the group consisting of: SEQ ID NO:1; SEQ ID NO:3; SEQ ID NO:5; SEQ ID NO:7; SEQ ID NO:17; SEQ ID NO:19; SEQ ID NO:21; SEQ ID NO:23; a nucleic acid sequence that is at least 95% homologous to SEQ ID NO:1; a nucleic acid sequence that is at least 95% homologous to SEQ ID NO:3; a nucleic acid sequence that is at least 95% homologous to SEQ ID NO:5; a nucleic acid sequence that is at least 95% homologous to SEQ ID NO:7; a nucleic acid sequence that is at least 95% homologous to SEQ ID NO:17; a nucleic acid sequence that is at least 95% homologous to SEQ ID NO:19; a nucleic acid sequence that is at least 95% homologous to SEQ ID NO:21; a nucleic acid sequence that is at least 95% homologous to SEQ ID NO:23; a fragment of SEQ ID NO:1; a fragment of SEQ ID NO:3; a fragment of SEQ ID NO:5; a fragment of SEQ ID NO:7; a fragment of SEQ ID NO:17; a fragment of SEQ ID NO:19; a fragment of SEQ ID NO:21; a fragment of SEQ ID NO:23; a nucleic acid sequence that is at least 95% homologous to a fragment of SEQ ID NO:1; a nucleic acid sequence that is at least 95% homologous to a fragment of SEQ ID NO:3; a nucleic acid sequence that is at least 95% homologous to a fragment of SEQ ID NO:5; a nucleic acid sequence that is at least 95% homologous to a fragment of SEQ ID NO:7; a nucleic acid sequence that is at least 95% homologous to a fragment of SEQ ID NO:17; a nucleic acid sequence that is at least 95% homologous to a fragment of SEQ ID NO:19; a nucleic acid sequence that is at least 95% homologous to a fragment of SEQ ID NO:21; and a nucleic acid sequence that is at least 95% homologous to a fragment of SEQ ID NO:23. In some embodiments, the nucleotide sequences encoding the HPV E6-E7 fusion antigen are without a leader sequence at 5' end that has nucleotide sequence SEQ ID NO:9.

The nucleotide sequences provided can be a plasmid.

In additional aspects, provided are pharmaceutical compositions comprising the disclosed nucleotide sequences; preferably with multiple antigens.

In some aspects, there are methods of inducing an effective immune response in an individual against more than one subtype of HPV, comprising administering to said individual a composition comprising one or more of the nucleotides sequences provided; preferably, the compositions have more than one antigen. The methods preferably include a step of introducing the provided nucleotide sequences into the individual by electroporation.

BRIEF DESCRIPTION OF THE DRAWINGS

FIG. 1A through FIG. 1C, depicts Phylogenetic trees based on neighbor-joining evaluation of E6 and E7 alignments (FIG. 1A and FIG. 1B, respectively). FIG. 1C depicts the consensus E6/E7 fusion sequence. Asterisks indicate location of consensus sequences on each tree.

FIG. 2A through FIG. 2B depicts the in vivo expression of p6E6E7 and p11E6E7. Gene products were isolated from lysed transfected 293-T cells, run through SDS-PAGE gel, and detected using autoradiography. Both HPV 6 and HPV 11 E6/E7 proteins are approximately 32 kDa each (FIG. 2A). Human rhabdomyosarcoma (RD) cells were also transfected with p6E6E7 and p11E6E7 and later fixed after immunofluorescence staining. FITC fluorescence confirms expression of p6E6E7 and p11E6E7(FIG. 2B). DAPI fluorescence confirms nuclei localization consequent of Hoescht staining.

FIG. 3A through FIG. 3B depicts IFN-γ ELISpot assays showing the induction of robust cell-mediated responses by p6E6E7 (FIG. 3A) and p11E6E7 (FIG. 3B) in C57BL/6 mice. Assays were performed using splenocytes isolated from mice in each respective group (5 mice per group) after three biweekly immunizations. Each immunization consisted of 20 μg per construct. Mice in combo group received both p6E6E7 and p11E6E7 at 20 μg per construct, for a total of 40 μg DNA per immunization. DNA was administered via IM injection, followed by electroporation (* denotes $p<0.0001$; † denotes $p=0.0001$).

FIG. 6 displays the amino acid sequence for HPV31 E6/E7 (SEQ ID NO:18) annotated to show the IgE leader sequence (IgEL), the endoproteolytic cleavage site, and sites where the E6 and E7 domain were mutated to enhance expression and immunogenicity.

FIG. 7 displays the amino acid sequence for HPV52 E6/E7 (SEQ ID NO:20) annotated to show the IgE leader sequence (IgEL), the endoproteolytic cleavage site, and sites where the E6 and E7 domain were mutated to enhance expression and immunogenicity.

DETAILED DESCRIPTION OF PREFERRED EMBODIMENTS

Figure 4A:
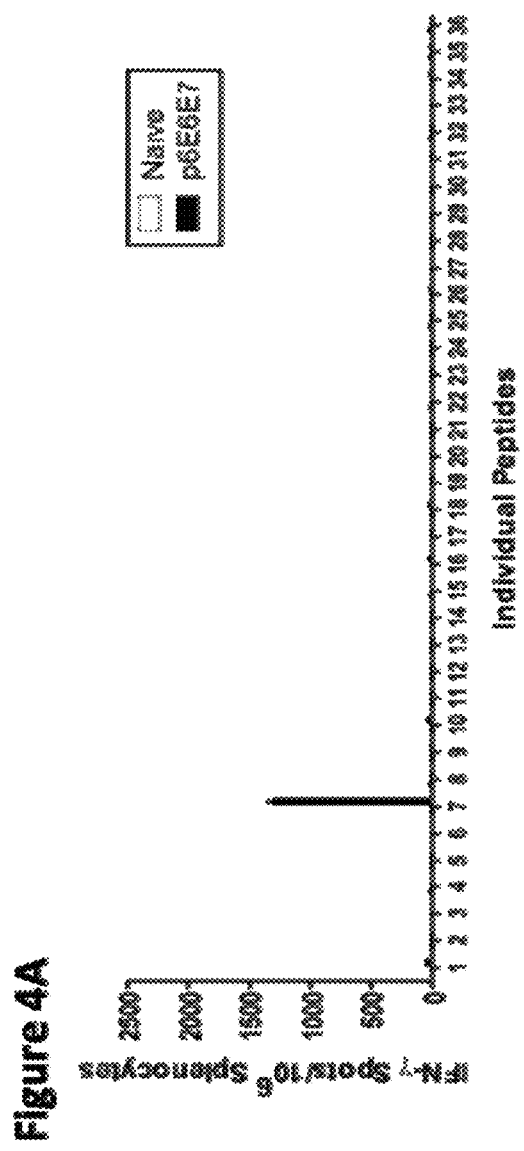
FIG. 4A through FIG. 4B depicts the additional IFN-γ ELISpot assays performed using individual peptides to characterize dominant epitopes. Splenocytes isolated from vaccinated mice and negative control were stimulated with overlapping peptides that span the entire HPV 6 E6/E7 fusion protein (FIG. 4A) or HPV 11 E6/E7 fusion protein (FIG. 4B).

Definitions.

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6,9, and 7.0 are explicitly contemplated.

a. Adjuvant

"Adjuvant" as used herein may mean any molecule added to the DNA plasmid vaccines described herein to enhance antigenicity of the one or more antigens encoded by the DNA plasmids and encoding nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Antigen

"Antigen" refers to: proteins having an HPV E6 or HPV E7 domain, and preferably and E6 and E7 fusion with an endeoproteolytic cleavage site therebetween. Antigens include SEQ ID NOs: 2 (subtype 6), 4 (subtype 11), 6 (subtype 33), 8 (subtype 58), 18 (subtype 31), 20 (subtype 52), 22 (subtype 16), and 24 (subtype 18); fragments thereof of lengths set forth herein, variants, i.e. proteins with sequences homologous to SEQ ID NOs:2, 4, 6, 8, 18, 20, 22, and 24 as set forth herein, fragments of variants having lengths set forth herein, and combinations thereof. Antigens may have an IgE leader sequence of SEQ ID NO:10 or may alternatively have such sequence removed from the N-terminal end. Antigens may optionally include signal peptides such as those from other proteins.

d. Coding Sequence

"Coding sequence" or "encoding nucleic acid" as used herein may mean refers to the nucleic acid (RNA or DNA molecule) that comprise a nucleotide sequence which encodes an antigen as set forth in section c. above. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides, e.g., an IgE leader sequence such as SEQ ID NO:9.

e. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

f. Fragment

"Fragment" may mean a polypeptide fragment of an antigen that is capable of eliciting an immune response in a mammal against the antigen. A fragment of an antigen may be 100% identical to the full length except missing at least one amino acid from the N and/or C terminal, in each case with or without signal peptides and/or a methionine at position 1. Fragments may comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antigen, excluding any heterologous signal peptide added. The fragment may, preferably, comprise a fragment of a polypeptide that is 95% or more, 96% or more, 97% or more, 98% or more or 99% or more homologous to the antigen and additionally comprise an N terminal methionine or heterologous signal peptide which is not included when calculating percent homology Fragments may further comprise an N terminal methionine and/or a signal peptide such as an immunoglobulin signal peptide, for example an IgE or IgG signal peptide. The N terminal methionine and/or signal peptide may be linked to a fragment of an antigen.

A fragment of a nucleic acid sequence that encodes antigen may be 100% identical to the full length except missing at least one nucleotide from the 5' and/or 3' end, in each case with or without sequences encoding signal peptides and/or a methionine at position 1. Fragments may comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may, preferably, comprise a fragment that encodes a polypeptide that is 95% or more, 96% or more, 97% or more, 98% or more or 99% or more homologous to the antigen and additionally optionally comprise sequence encoding an N terminal methionine or heterologous signal peptide which is not included when calculating percent homology Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

g. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

h. Immune Response

"Immune response" as used herein may mean the activation of a host's immune system, e.g., that of a mammal, in response to the introduction of one or more antigens via the provided DNA plasmid vaccines. The immune response can be in the form of a cellular or humoral response, or both.

i. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

j. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

k. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

l. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5 10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0

M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

m. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

n. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

o. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

p. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Improved vaccines are disclosed which arise from a multi-phase strategy to enhance cellular immune responses induced by immunogens. Modified consensus sequences were generated. Genetic modifications including codon optimization, RNA optimization, and the addition of a high efficient immunoglobin leader sequence are also disclosed. The novel construct has been designed to elicit stronger and broader cellular immune responses than a corresponding codon optimized immunogens.

The improved HPV vaccines are based upon proteins and genetic constructs that encode proteins with epitopes that make them particularly effective as immunogens against which anti-HPV can be induced. Accordingly, vaccines may induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments, a vaccine is delivered to an individual to modulate the activity of the individual's immune system and thereby enhance the immune response against HPV. When a nucleic acid molecule that encodes the protein is taken up by cells of the individual the nucleotide sequence is expressed in the cells and the protein are thereby delivered to the individual. Methods of delivering the coding sequences of the protein on nucleic acid molecule such as plasmid, as part of recombinant vaccines and as part of attenuated vaccines, as isolated proteins or proteins part of a vector are provided.

Compositions and methods are provided which prophylactically and/or therapeutically immunize an individual against HPV.

Compositions for delivering nucleic acid molecules that comprise a nucleotide sequence that encodes the immunogen are operably linked to regulatory elements. Compositions may include a plasmid that encodes the immunogen, a recombinant vaccine comprising a nucleotide sequence that encodes the immunogen, a live attenuated pathogen that encodes a protein of the invention and/or includes a protein of the invention; a killed pathogen includes a protein of the invention; or a composition such as a liposome or subunit vaccine that comprises a protein of the invention. The present invention further relates to injectable pharmaceutical compositions that comprise compositions.

Aspects of the invention provide compositions comprising at least one nucleotide sequence comprising an HPV E6-E7 fusion antigen selected from the group consisting of: HPV6, HPV11, HPV16, HPV18, HPV31, HPV33, HPV39, HPV45, HPV52, and HPV58. In some embodiments the compositions can comprise HPV6, HPV11, HPV16, HPV18, HPV31, HPV33, HPV52, and HPV58. In some embodiments the compositions can comprise HPV16, HPV18, HPV31, HPV33, HPV52, and HPV58. In some embodiments the compositions can comprise HPV6, HPV11, HPV16, and HPV18. In some embodiments the compositions can comprise HPV16, HPV31, and HPV52.

Another aspect provides compositions comprising one or more nucleotide sequences encoding an HPV E6-E7 fusion antigen selected from the group consisting of: nucleotide sequence that encodes SEQ ID NO:2; nucleotide sequence that encodes SEQ ID NO:4; nucleotide sequence that encodes SEQ ID NO:6; nucleotide sequence that encodes SEQ ID NO:8; nucleotide sequence that encodes SEQ ID NO:18; nucleotide sequence that encodes SEQ ID NO:20; nucleotide sequence that encodes SEQ ID NO:22; nucleotide sequence that encodes SEQ ID NO:24; nucleotide sequence that encodes SEQ ID NO:25; nucleotide sequence that encodes SEQ ID NO:26; a nucleic acid sequence that is at least 95% homologous to a nucleic acid sequence nucleotide sequence that encodes SEQ ID NO:2; a nucleic acid sequence that is at least 95% homologous to a nucleotide sequence that encodes SEQ ID NO:4; a nucleic acid sequence that is at least 95% homologous to a nucleotide sequence that encodes SEQ ID NO:6; a nucleic acid sequence that is at least 95% homologous to a nucleotide sequence that encodes SEQ ID NO:8; a nucleic acid sequence that is at least 95% homologous to a nucleotide sequence that encodes SEQ ID NO:18; a nucleic acid sequence that is at least 95% homologous to a nucleotide sequence that encodes SEQ ID NO:20; a nucleic acid sequence that is at least 95% homologous to a nucleotide sequence that encodes SEQ ID NO:22; a nucleic acid sequence that is at least 95% homologous to a nucleotide sequence that encodes SEQ ID NO:24; a nucleic acid sequence that is at least 95% homologous to a nucleotide sequence that encodes SEQ ID NO:25; a nucleic acid sequence that is at least 95% homologous to a nucleotide sequence that encodes SEQ ID NO:26; a fragment of a nucleotide sequence that encodes SEQ ID NO:2; a fragment of a nucleotide sequence that encodes SEQ ID NO:4; a fragment of a nucleotide sequence that encodes SEQ ID NO:6; a fragment of a nucleotide sequence that encodes SEQ ID NO:8; a fragment of a nucleotide sequence that encodes SEQ ID NO:18; a fragment of a nucleotide sequence that encodes SEQ ID NO:20; a fragment of a nucleotide sequence that encodes SEQ ID NO:22; a fragment of a nucleotide sequence that encodes SEQ ID NO:24; a fragment of a nucleotide sequence that encodes SEQ ID NO:25; a fragment of a nucleotide sequence that encodes SEQ ID NO:26; a nucleic acid sequence that is at least 95% homologous to a fragment of a nucleotide sequence that encodes SEQ ID NO:2; a nucleic acid sequence that is at least 95% homologous to a fragment of a nucleotide sequence that encodes SEQ ID NO:4; a nucleic acid sequence that is at least 95% homologous to a fragment of a nucleotide sequence that encodes SEQ ID NO:6; a nucleic acid sequence that is at least 95% homologous to a fragment of a nucleotide sequence that encodes SEQ ID NO:8; a nucleic acid sequence that is at least 95% homologous to a fragment of a nucleotide sequence that encodes SEQ ID NO:18; a nucleic acid sequence that is at least 95% homologous to a fragment of a nucleotide sequence that encodes SEQ ID NO:20; a nucleic acid sequence that is at least 95% homologous to a fragment of a nucleotide sequence that encodes SEQ ID NO:22; a nucleic acid sequence that is at least 95% homologous to a fragment of a nucleotide sequence that encodes SEQ ID NO:24; a nucleic acid sequence that is at least 95% homologous to a fragment of a nucleotide sequence that encodes SEQ ID NO:25; and a nucleic acid sequence that is at least 95% homologous to a fragment of a nucleotide sequence that encodes SEQ ID NO:26.

In some embodiments the compositions include HPV E6-E7 fusion antigens selected from the group consisting of: nucleotide sequence that encodes SEQ ID NO:2; nucleotide sequence that encodes SEQ ID NO:4; nucleotide sequence that encodes SEQ ID NO:6; nucleotide sequence that encodes SEQ ID NO:8; nucleotide sequence that encodes SEQ ID NO:18; nucleotide sequence that encodes SEQ ID NO:20; nucleotide sequence that encodes SEQ ID NO:22; nucleotide sequence that encodes SEQ ID NO:24; a nucleic acid sequence that is at least 95% homologous to a nucleic acid sequence nucleotide sequence that encodes SEQ ID NO:2; a nucleic acid sequence that is at least 95% homologous to a nucleotide sequence that encodes SEQ ID NO:4; a nucleic acid sequence that is at least 95% homologous to a nucleotide sequence that encodes SEQ ID NO:6; a nucleic acid sequence that is at least 95% homologous to a nucleotide sequence that encodes SEQ ID NO:8; a nucleic acid sequence that is at least 95% homologous to a nucleotide sequence that encodes SEQ ID NO:18; a nucleic acid sequence that is at least 95% homologous to a nucleotide sequence that encodes SEQ ID NO:20; a nucleic acid sequence that is at least 95% homologous to a nucleotide sequence that encodes SEQ ID NO:22; a nucleic acid sequence that is at least 95% homologous to a nucleotide sequence that encodes SEQ ID NO:24; a fragment of a nucleotide sequence that encodes SEQ ID NO:2; a fragment of a nucleotide sequence that encodes SEQ ID NO:4; a fragment of a nucleotide sequence that encodes SEQ ID NO:6; a fragment of a nucleotide sequence that encodes SEQ ID NO:8; a fragment of a nucleotide sequence that encodes SEQ ID NO:18; a fragment of a nucleotide sequence that encodes SEQ ID NO:20; a fragment of a nucleotide sequence that encodes SEQ ID NO:22; a fragment of a nucleotide sequence that encodes SEQ ID NO:24; a nucleic acid sequence that is at least 95% homologous to a fragment of a nucleotide sequence that encodes SEQ ID NO:2; a nucleic acid sequence that is at least 95% homologous to a fragment of a nucleotide sequence that encodes SEQ ID NO:4; a nucleic acid sequence that is at least 95% homologous to a fragment of a nucleotide sequence that encodes SEQ ID NO:6; a nucleic acid sequence that is at least 95% homologous to a fragment of a nucleotide sequence that encodes SEQ ID NO:8; a nucleic acid sequence that is at least 95% homologous to a fragment of a nucleotide sequence that encodes SEQ ID NO:18; a nucleic acid sequence that is at least 95% homologous to a fragment of a nucleotide sequence that encodes SEQ ID NO:20; a nucleic acid sequence that is at least 95% homologous to a fragment of a nucleotide sequence that encodes SEQ ID NO:22; and a nucleic acid sequence that is at least 95% homologous to a fragment of a nucleotide sequence that encodes SEQ ID NO:24.

In some embodiments the compositions include HPV E6-E7 fusion antigens selected from the group consisting of: nucleotide sequence that encodes SEQ ID NO:6; nucleotide sequence that encodes SEQ ID NO:8; nucleotide sequence that encodes SEQ ID NO:18; nucleotide sequence that encodes SEQ ID NO:20; nucleotide sequence that encodes SEQ ID NO:22; nucleotide sequence that encodes SEQ ID NO:24; a nucleic acid sequence that is at least 95% homologous to a nucleotide sequence that encodes SEQ ID NO:6; a nucleic acid sequence that is at least 95% homologous to a nucleotide sequence that encodes SEQ ID NO:8; a nucleic acid sequence that is at least 95% homologous to a nucleotide sequence that encodes SEQ ID NO:18; a nucleic acid sequence that is at least 95% homologous to a nucleotide sequence that encodes SEQ ID NO:20; a nucleic acid sequence that is at least 95% homologous to a nucleotide sequence that encodes SEQ ID NO:22; a nucleic acid sequence that is at least 95% homologous to a nucleotide sequence that encodes SEQ ID NO:24; a fragment of a nucleotide sequence that encodes SEQ ID NO:6; a fragment of a nucleotide sequence that encodes SEQ ID NO: 8; a fragment of a nucleotide sequence that encodes SEQ ID NO:18; a fragment of a nucleotide sequence that encodes SEQ ID NO:20; a fragment of a nucleotide sequence that encodes SEQ ID NO:22; a fragment of a nucleotide sequence that encodes SEQ ID NO:24; a nucleic acid sequence that is at least 95% homologous to a fragment of a nucleotide sequence that encodes SEQ ID NO:6; a nucleic acid sequence that is at least 95% homologous to a fragment of a nucleotide sequence that encodes SEQ ID NO:8; a nucleic acid sequence that is at least 95% homologous to a fragment of a nucleotide sequence that encodes SEQ ID NO:18; a nucleic acid sequence that is at least 95% homologous to a fragment of a nucleotide sequence that encodes SEQ ID NO:20; a nucleic acid sequence that is at least 95% homologous to a fragment of a nucleotide sequence that encodes SEQ ID NO:22; and a nucleic acid sequence that is at least 95% homologous to a fragment of a nucleotide sequence that encodes SEQ ID NO:24.

In some embodiments the compositions include HPV E6-E7 fusion antigens selected from the group consisting of: nucleotide sequence that encodes SEQ ID NO:2; nucleotide sequence that encodes SEQ ID NO:4; nucleotide sequence that encodes SEQ ID NO:22; nucleotide sequence that encodes SEQ ID NO:24; a nucleic acid sequence that is at least 95% homologous to a nucleic acid sequence nucleotide sequence that encodes SEQ ID NO:2; a nucleic acid sequence that is at least 95% homologous to a nucleotide sequence that encodes SEQ ID NO:4; a nucleic acid sequence that is at least 95% homologous to a nucleotide sequence that encodes SEQ ID NO:22; a nucleic acid sequence that is at least 95% homologous to a nucleotide sequence that encodes SEQ ID NO:24; a fragment of a nucleotide sequence that encodes SEQ ID NO:2; a fragment of a nucleotide sequence that encodes SEQ ID NO:4; a fragment of a nucleotide sequence that encodes SEQ ID NO:22; a fragment of a nucleotide sequence that encodes SEQ ID NO:24; a nucleic acid sequence that is at least 95% homologous to a fragment of a nucleotide sequence that encodes SEQ ID NO:2; a nucleic acid sequence that is at least 95% homologous to a fragment of a nucleotide sequence that encodes SEQ ID NO:4; a nucleic acid sequence that is at least 95% homologous to a fragment of a nucleotide sequence that encodes SEQ ID NO:22; and a nucleic acid sequence that is at least 95% homologous to a fragment of a nucleotide sequence that encodes SEQ ID NO:24.

In some embodiments the compositions include HPV E6-E7 fusion antigens selected from the group consisting of: nucleotide sequence that encodes SEQ ID NO:18; nucleotide sequence that encodes SEQ ID NO:20; nucleotide sequence that encodes SEQ ID NO:22; a nucleic acid sequence that is at least 95% homologous to a nucleotide sequence that encodes SEQ ID NO:18; a nucleic acid sequence that is at least 95% homologous to a nucleotide sequence that encodes SEQ ID NO:20; a nucleic acid sequence that is at least 95% homologous to a nucleotide sequence that encodes SEQ ID NO:22; a fragment of a nucleotide sequence that encodes SEQ ID NO:18; a fragment of a nucleotide sequence that encodes SEQ ID NO:20; a fragment of a nucleotide sequence that encodes SEQ ID NO:22; a nucleic acid sequence that is at least 95% homologous to a fragment of a nucleotide sequence that encodes SEQ ID NO:18; a nucleic acid sequence that is at least 95% homologous to a fragment of a nucleotide sequence that encodes SEQ ID NO:20; and a nucleic acid sequence that is at least 95% homologous to a fragment of a nucleotide sequence that encodes SEQ ID NO:22.

In another aspect of the invention, there are provided compositions comprising one or more nucleotide sequences encoding an HPV E6-E7 fusion antigen selected from the group consisting of: SEQ ID NO:1; SEQ ID NO:3; SEQ ID NO:5; SEQ ID NO:7; SEQ ID NO:17; SEQ ID NO:19; SEQ ID NO:21; SEQ ID NO:23; a nucleic acid sequence that is at least 95% homologous to SEQ ID NO:1; a nucleic acid sequence that is at least 95% homologous to SEQ ID NO:3; a nucleic acid sequence that is at least 95% homologous to SEQ ID NO:5; a nucleic acid sequence that is at least 95% homologous to SEQ ID NO:7; a nucleic acid sequence that is at least 95% homologous to SEQ ID NO:17; a nucleic acid sequence that is at least 95% homologous to SEQ ID NO:19; a nucleic acid sequence that is at least 95% homologous to SEQ ID NO:21; a nucleic acid sequence that is at least 95% homologous to SEQ ID NO:23; a fragment of SEQ ID NO:1; a fragment of SEQ ID NO:3; a fragment of SEQ ID NO:5; a fragment of SEQ ID NO:7; a fragment of SEQ ID NO:17; a fragment of SEQ ID NO:19; a fragment of SEQ ID NO:21; a fragment of SEQ ID NO:23; a nucleic acid sequence that is at least 95% homologous to a fragment of SEQ ID NO:1; a nucleic acid sequence that is at least 95% homologous to a fragment of SEQ ID NO:3; a nucleic acid sequence that is at least 95% homologous to a fragment of SEQ ID NO:5; a nucleic acid sequence that is at least 95% homologous to a fragment of SEQ ID NO:7; a nucleic acid sequence that is at least 95% homologous to a fragment of SEQ ID NO:17; a nucleic acid sequence that is at least 95% homologous to a fragment of SEQ ID NO:19; a nucleic acid sequence that is at least 95% homologous to a fragment of SEQ ID NO:21; and a nucleic acid sequence that is at least 95% homologous to a fragment of SEQ ID NO:23.

In some embodiments the compositions include HPV E6-E7 fusion antigens selected from the group consisting of: SEQ ID NO:5; SEQ ID NO:7; SEQ ID NO:17; SEQ ID NO:19; SEQ ID NO:21; SEQ ID NO:23; a nucleic acid sequence that is at least 95% homologous to SEQ ID NO:5; a nucleic acid sequence that is at least 95% homologous to SEQ ID NO:7; a nucleic acid sequence that is at least 95% homologous to SEQ ID NO:17; a nucleic acid sequence that is at least 95% homologous to SEQ ID NO:19; a nucleic acid sequence that is at least 95% homologous to SEQ ID NO:21; a nucleic acid sequence that is at least 95% homologous to SEQ ID NO:23; a fragment of SEQ ID NO:5; a fragment of SEQ ID NO:7; a fragment of SEQ ID NO:17; a fragment of SEQ ID NO:19; a fragment of SEQ ID NO:21; a fragment of SEQ ID NO:23; a nucleic acid sequence that is at least 95% homologous to a fragment of SEQ ID NO:5; a nucleic acid sequence that is at least 95% homologous to a fragment of SEQ ID NO:7; a nucleic acid sequence that is at least 95% homologous to a fragment of SEQ ID NO:17; a nucleic acid sequence that is at least 95% homologous to a fragment of SEQ ID NO:19; a nucleic acid sequence that is at least 95% homologous to a fragment of SEQ ID NO:21; and a nucleic acid sequence that is at least 95% homologous to a fragment of SEQ ID NO:23.

In some embodiments the compositions include HPV E6-E7 fusion antigens selected from the group consisting of: SEQ ID NO:1; SEQ ID NO:3; SEQ ID NO:21; SEQ ID NO:23; a nucleic acid sequence that is at least 95% homologous to SEQ ID NO:1; a nucleic acid sequence that is at least 95% homologous to SEQ ID NO:3; a nucleic acid sequence that is at least 95% homologous to SEQ ID NO:21; a nucleic acid sequence that is at least 95% homologous to SEQ ID NO:23; a fragment of SEQ ID NO:1; a fragment of SEQ ID NO:3; a fragment of SEQ ID NO:21; a fragment of SEQ ID NO:23; a nucleic acid sequence that is at least 95% homologous to a fragment of SEQ ID NO:1; a nucleic acid sequence that is at least 95% homologous to a fragment of SEQ ID NO:3; a nucleic acid sequence that is at least 95% homologous to a fragment of SEQ ID NO:21; and a nucleic acid sequence that is at least 95% homologous to a fragment of SEQ ID NO:23.

In some embodiments the compositions include HPV E6-E7 fusion antigens selected from the group consisting of: SEQ ID NO:17; SEQ ID NO:19; SEQ ID NO:21; a nucleic acid sequence that is at least 95% homologous to SEQ ID NO:17; a nucleic acid sequence that is at least 95% homologous to SEQ ID NO:19; a nucleic acid sequence that is at least 95% homologous to SEQ ID NO:21; a fragment of SEQ ID NO:17; a fragment of SEQ ID NO:19; a fragment of SEQ ID NO:21; nucleic acid sequence that is at least 95% homologous to a fragment of SEQ ID NO:17; a nucleic acid sequence that is at least 95% homologous to a fragment of SEQ ID NO:19; and a nucleic acid sequence that is at least 95% homologous to a fragment of SEQ ID NO:21.

In some embodiments the nucleotide sequences described herein is absent the leader sequence. The nucleotide sequences comprising HPV6, HPV11, HPV16, HPV18, HPV31, HPV33, HPV39, HPV45, HPV52, and HPV58 is absent a leader sequence. In particular, the HPV E6-E7 fusion antigens including nucleotide sequence that encodes SEQ ID NO:2; nucleotide sequence that encodes SEQ ID NO:4; nucleotide sequence that encodes SEQ ID NO:6; nucleotide sequence that encodes SEQ ID NO:8; nucleotide sequence that encodes SEQ ID NO:18; nucleotide sequence that encodes SEQ ID NO:20; nucleotide sequence that encodes SEQ ID NO:22; nucleotide sequence that encodes SEQ ID NO:24; and nucleotide sequence that encodes SEQ ID NO:25 are absent a leader sequence at 5' end, for example nucleotide sequence encoding SEQ ID NO. 10. In particular, the HPV E6-E7 fusion antigens including nucleotide sequence SEQ ID NO:1; SEQ ID NO:3; SEQ ID NO:5; SEQ ID NO:7; SEQ ID NO:17; SEQ ID NO:19; SEQ ID NO:21; SEQ ID NO:23 are absent a leader sequence at 5' end, for example nucleotide sequence SEQ ID NO. 9.

In some embodiments the nucleotide sequences of the present invention can be 80%, 81%, 82%, 83%, 84%, 85%, 86%, 87%, 88%, 89%, 90%, 91%, 92%, 93%, 94%, 95%, 96%, 97%, 98%, or 99% homologous with the provided nucleotide sequences; preferably 95%, 96%, 97%, 98%, or 99%; or 98% or 99%.

The nucleotide sequences provided can be included into one of a variety of known vectors or delivery systems, including a plasmid, viral vector, lipid vector, nanoparticle; preferably a plasmid.

In additional aspects, provided are pharmaceutical compositions comprising the disclosed nucleotide sequences; preferably with multiple antigens.

In some aspects, there are methods of inducing an effective immune response in an individual against more than one subtype of HPV, comprising administering to said individual a composition comprising one or more of the nucleotides sequences provided; preferably, the compositions have more than one antigen. The methods preferably include a step of introducing the provided nucleotide sequences into the individual by electroporation.

SEQ ID NO:1 comprises a nucleotide sequence that encodes a consensus immunogen of HPV 6 E6 and E7 proteins. SEQ ID NO:1 includes an IgE leader sequence SEQ ID NO:9 linked to the nucleotide sequence at the 5' end of SEQ ID NO:1. SEQ ID NO:2 comprises the amino acid sequence for the consensus immunogen of HPV 6 E6 and E7 proteins. SEQ ID NO:2 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:2, or a nucleic acid molecule that encodes SEQ ID NO:2.

Fragments of SEQ ID NO:2 may be 100% identical to the full length except missing at least one amino acid from the N and/or C terminal, in each case with or without signal peptides and/or a methionine at position 1. Fragments of SEQ ID NO:2 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:2, excluding any heterologous signal peptide added. The fragment can, preferably, comprise a fragment of SEQ ID NO:2 that is 95% or more, 96% or more, 97% or more, 98% or more or 99% or more homologous to SEQ ID NO:2 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:1 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:1, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:2 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment.

In some embodiments, fragments of SEQ ID NO:1 may comprise 786 or more nucleotides; in some embodiments, 830 or more nucleotides; in some embodiments 856 or more nucleotides; and in some embodiments, 865 or more nucleotides. In some embodiments, fragments of SEQ ID NO:1 such as those set forth herein may further comprise coding sequences for the IgE leader sequences. In some embodiments, fragments of SEQ ID NO:1 do not comprise coding sequences for the IgE leader sequences.

In some embodiments, fragments of SEQ ID NO:2 may comprise 252 or more amino acids; in some embodiments, 266 or more amino acids; in some embodiments, 275 or more amino acids; and in some embodiments, 278 or more amino acids.

SEQ ID NO:3 comprises a nucleotide sequence that encodes a consensus immunogen of HPV 11 E6 and E7 proteins. SEQ ID NO:3 includes an IgE leader sequence SEQ ID NO:9 linked to the nucleotide sequence at the 5' end of SEQ ID NO:3. SEQ ID NO:4 comprises the amino acid sequence for the consensus immunogen of HPV 11 E6 and E7 proteins. SEQ ID NO:4 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:4, or a nucleic acid molecule that encodes SEQ ID NO:4.

Fragments of SEQ ID NO:4 may be 100% identical to the full length except missing at least one amino acid from the N and/or C terminal, in each case with or without signal peptides and/or a methionine at position 1. Fragments of SEQ ID NO:4 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:4, excluding any heterologous signal peptide added. The fragment can, preferably, comprise a fragment of SEQ ID NO:4 that is 95% or more, 96% or more, 97% or more, 98% or more or 99% or more homologous to SEQ ID NO:4 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:3 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:3, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:4 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment.

In some embodiments, fragments of SEQ ID NO:3 may comprise 786 or more nucleotides; in some embodiments, 830 or more nucleotides; in some embodiments 856 or more nucleotides; and in some embodiments, 865 or more nucleotides. In some embodiments, fragments of SEQ ID NO:3 such as those set forth herein may further comprise coding sequences for the IgE leader sequences. In some embodiments, fragments of SEQ ID NO:3 do not comprise coding sequences for the IgE leader sequences.

In some embodiments, fragments of SEQ ID NO:4 may comprise 252 or more amino acids; in some embodiments, 266 or more amino acids; in some embodiments, 275 or more amino acids; and in some embodiments, 278 or more amino acids.

SEQ ID NO:5 comprises a nucleotide sequence that encodes a consensus immunogen of HPV 33 E6 and E7 proteins. SEQ ID NO:5 includes an IgE leader sequence SEQ ID NO:9 linked to the nucleotide sequence at the 5' end of SEQ ID NO:5. SEQ ID NO:6 comprises the amino acid sequence for the consensus immunogen of HPV 33 E6 and E7 proteins. SEQ ID NO:6 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:6, or a nucleic acid molecule that encodes SEQ ID NO:6.

Fragments of SEQ ID NO:6 may be 100% identical to the full length except missing at least one amino acid from the N and/or C terminal, in each case with or without signal peptides and/or a methionine at position 1. Fragments of SEQ ID NO:6 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:6, excluding any heterologous signal peptide added. The fragment can, preferably, comprise a fragment of SEQ ID NO:6 that is 95% or more, 96% or more, 97% or more, 98% or more or 99% or more homologous to SEQ ID NO:6 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:5 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:5, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:6 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment.

In some embodiments, fragments of SEQ ID NO:5 may comprise 746 or more nucleotides; in some embodiments, 787 or more nucleotides; in some embodiments 812 or more nucleotides; and in some embodiments, 820 or more nucleotides. In some embodiments, fragments of SEQ ID NO:5 such as those set forth herein may further comprise coding sequences for the IgE leader sequences. In some embodiments, fragments of SEQ ID NO:5 do not comprise coding sequences for the IgE leader sequences.

In some embodiments, fragments of SEQ ID NO:6 may comprise 235 or more amino acids; in some embodiments, 248 or more amino acids; in some embodiments, 256 or more amino acids; and in some embodiments, 259 or more amino acids.

SEQ ID NO:7 comprises a nucleotide sequence that encodes a consensus immunogen of HPV 58 E6 and E7 proteins. SEQ ID NO:7 includes an IgE leader sequence SEQ ID NO:9 linked to the nucleotide sequence at the 5' end of SEQ ID NO:7. SEQ ID NO:8 comprises the amino acid sequence for the consensus immunogen of HPV 58 E6 and E7 proteins. SEQ ID NO:8 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:8, or a nucleic acid molecule that encodes SEQ ID NO:8.

Fragments of SEQ ID NO:8 may be 100% identical to the full length except missing at least one amino acid from the N and/or C terminal, in each case with or without signal peptides and/or a methionine at position 1. Fragments of SEQ ID NO:8 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:8, excluding any heterologous signal peptide added. The fragment can, preferably, comprise a fragment of SEQ ID NO:8 that is 95% or more, 96% or more, 97% or more, 98% or more or 99% or more homologous to SEQ ID NO:8 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:7 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:7, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:8 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment.

In some embodiments, fragments of SEQ ID NO:7 may comprise 752 or more nucleotides; in some embodiments, 794 or more nucleotides; in some embodiments 819 or more nucleotides; and in some embodiments, 827 or more nucleotides. In some embodiments, fragments of SEQ ID NO:7 such as those set forth herein may further comprise coding sequences for the IgE leader sequences. In some embodiments, fragments of SEQ ID NO:7 do not comprise coding sequences for the IgE leader sequences.

In some embodiments, fragments of SEQ ID NO:8 may comprise 235 or more amino acids; in some embodiments, 249 or more amino acids; in some embodiments, 257 or more amino acids; and in some embodiments, 260 or more amino acids.

SEQ ID NO:17 comprises a nucleotide sequence that encodes a consensus immunogen of HPV 31 E6 and E7 proteins. SEQ ID NO:17 includes an IgE leader sequence SEQ ID NO:9 linked to the nucleotide sequence at the 5' end of SEQ ID NO:17. SEQ ID NO:18 comprises the amino acid sequence for the consensus immunogen of HPV 31 E6 and E7 proteins. SEQ ID NO:18 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:18, or a nucleic acid molecule that encodes SEQ ID NO:18.

Fragments of SEQ ID NO:18 may be 100% identical to the full length except missing at least one amino acid from the N and/or C terminal, in each case with or without signal peptides and/or a methionine at position 1. Fragments of SEQ ID NO:18 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:18, excluding any heterologous signal peptide added. The fragment can, preferably, comprise a fragment of SEQ ID NO:18 that is 95% or more, 96% or more, 97% or more, 98% or more or 99% or more homologous to SEQ ID NO:18 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:17 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:17, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:18 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment.

In some embodiments, fragments of SEQ ID NO:17 may comprise 713 or more nucleotides; in some embodiments, 752 or more nucleotides; in some embodiments 776 or more nucleotides; and in some embodiments, 784 or more nucleotides. In some embodiments, fragments of SEQ ID NO:17 such as those set forth herein may further comprise coding sequences for the IgE leader sequences. In some embodiments, fragments of SEQ ID NO:17 do not comprise coding sequences for the IgE leader sequences.

In some embodiments, fragments of SEQ ID NO:18 may comprise 236 or more amino acids; in some embodiments, 249 or more amino acids; in some embodiments, 257 or more amino acids; and in some embodiments, 259 or more amino acids.

SEQ ID NO:19 comprises a nucleotide sequence that encodes a consensus immunogen of HPV 52 E6 and E7 proteins. SEQ ID NO:19 includes an IgE leader sequence SEQ ID NO:9 linked to the nucleotide sequence at the 5' end of SEQ ID NO:19. SEQ ID NO:20 comprises the amino acid sequence for the consensus immunogen of HPV 52 E6 and E7 proteins. SEQ ID NO:20 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:20, or a nucleic acid molecule that encodes SEQ ID NO:20.

Fragments of SEQ ID NO:20 may be 100% identical to the full length except missing at least one amino acid from the N and/or C terminal, in each case with or without signal peptides and/or a methionine at position 1. Fragments of SEQ ID NO:20 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:20, excluding any heterologous signal peptide added. The fragment can, preferably, comprise a fragment of SEQ ID NO:20 that is 95% or more, 96% or more, 97% or more, 98% or more or 99% or more homologous to SEQ ID NO:20 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:19 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:19, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:20 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment.

In some embodiments, fragments of SEQ ID NO:19 may comprise 713 or more nucleotides; in some embodiments, 752 or more nucleotides; in some embodiments 776 or more nucleotides; and in some embodiments, 784 or more nucleotides. In some embodiments, fragments of SEQ ID NO:19 such as those set forth herein may further comprise coding sequences for the IgE leader sequences. In some embodiments, fragments of SEQ ID NO:19 do not comprise coding sequences for the IgE leader sequences.

In some embodiments, fragments of SEQ ID NO:20 may comprise 236 or more amino acids; in some embodiments, 249 or more amino acids; in some embodiments, 257 or more amino acids; and in some embodiments, 259 or more amino acids.

SEQ ID NO:21 comprises a nucleotide sequence that encodes a consensus immunogen of HPV16 E6 and E7 proteins. SEQ ID NO:21 includes an IgE leader sequence SEQ ID NO:9 linked to the nucleotide sequence at the 5' end of SEQ ID NO:21. SEQ ID NO:22 comprises the amino acid sequence for the consensus immunogen of HPV16 E6 and E7 proteins. SEQ ID NO:22 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:22, or a nucleic acid molecule that encodes SEQ ID NO:22.

Fragments of SEQ ID NO:22 may be 100% identical to the full length except missing at least one amino acid from the N and/or C terminal, in each case with or without signal peptides and/or a methionine at position 1. Fragments of SEQ ID NO:22 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:22, excluding any heterologous signal peptide added. The fragment can, preferably, comprise a fragment of SEQ ID NO:22 that is 95% or more, 96% or more, 97% or more, 98% or more or 99% or more homologous to SEQ ID NO:22 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:21 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:21, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:22 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment.

In some embodiments, fragments of SEQ ID NO:21 may comprise 736 or more nucleotides; in some embodiments, 777 or more nucleotides; in some embodiments 802 or more nucleotides; and in some embodiments, 810 or more nucleotides. In some embodiments, fragments of SEQ ID NO:21 such as those set forth herein may further comprise coding sequences for the IgE leader sequences. In some embodiments, fragments of SEQ ID NO:21 do not comprise coding sequences for the IgE leader sequences.

In some embodiments, fragments of SEQ ID NO:22 may comprise 238 or more amino acids; in some embodiments, 251 or more amino acids; in some embodiments, 259 or more amino acids; and in some embodiments, 261 or more amino acids.

SEQ ID NO:23 comprises a nucleotide sequence that encodes a consensus immunogen of HPV18 E6 and E7 proteins. SEQ ID NO:23 includes an IgE leader sequence SEQ ID NO:9 linked to the nucleotide sequence at the 5' end of SEQ ID NO:23. SEQ ID NO:24 comprises the amino acid sequence for the consensus immunogen of HPV18 E6 and E7 proteins. SEQ ID NO:24 includes an IgE leader sequence SEQ ID NO:10 at the N-terminal end of the consensus immunogen sequence. The IgE leader sequence is SEQ ID NO:10 and can be encoded by SEQ ID NO:9.

In some embodiments, vaccines include SEQ ID NO:24, or a nucleic acid molecule that encodes SEQ ID NO:24.

Fragments of SEQ ID NO:24 may be 100% identical to the full length except missing at least one amino acid from the N and/or C terminal, in each case with or without signal peptides and/or a methionine at position 1. Fragments of SEQ ID NO:24 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:24, excluding any heterologous signal peptide added. The fragment can, preferably, comprise a fragment of SEQ ID NO:24 that is 95% or more, 96% or more, 97% or more, 98% or more or 99% or more homologous to SEQ ID NO:24 and additionally comprise an N terminal methionine or heterologous signal peptide which is not included when calculating percent homology Fragments can further comprise an N terminal methionine and/or a signal peptide such as an immunoglobulin signal peptide, for example an IgE or IgG signal peptide. The N terminal methionine and/or signal peptide may be linked to the fragment.

Fragments of a nucleic acid sequence SEQ ID NO:23 can be 100% identical to the full length except missing at least one nucleotide from the 5' and/or 3' end, in each case with or without sequences encoding signal peptides and/or a methionine at position 1. Fragments can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of full length coding sequence SEQ ID NO:23, excluding any heterologous signal peptide added. The fragment can, preferably, comprise a fragment that encodes a polypeptide that is 95% or more, 96% or more, 97% or more, 98% or more or 99% or more homologous to the antigen SEQ ID NO:24 and additionally optionally comprise sequence encoding an N terminal methionine or heterologous signal peptide which is not included when calculating percent homology Fragments can further comprise coding sequences for an N terminal methionine and/or a signal peptide such as an immunoglobulin signal peptide, for example an IgE or IgG signal peptide. The coding sequence encoding the N terminal methionine and/or signal peptide may be linked to the fragment In some embodiments, fragments of SEQ ID NO:23 may comprise 705 or more nucleotides; in some embodiments, 744 or more nucleotides; in some embodiments 767 or more nucleotides; and in some embodiments, 775 or more nucleotides. In some embodiments, fragments of SEQ ID NO:23 such as those set forth herein may further comprise coding sequences for the IgE leader sequences. In some embodiments, fragments of SEQ ID NO:23 do not comprise coding sequences for the IgE leader sequences.

In some embodiments, fragments of SEQ ID NO:24 may comprise 234 or more amino acids; in some embodiments, 247 or more amino acids; in some embodiments, 255 or more amino acids; and in some embodiments, 257 or more amino acids.

SEQ ID NO:25 comprises the amino acid sequence for the consensus immunogen of HPV45 E6 and E7 proteins. SEQ ID NO:25 includes an IgE leader sequence SEQ ID NO:10 at the N-terminal end of the consensus immunogen sequence. The IgE leader sequence is SEQ ID NO:10 and can be encoded by SEQ ID NO:9.

SEQ ID NO:26 comprises the amino acid sequence for the consensus immunogen of HPV39 E6 and E7 proteins. SEQ ID NO:26 includes an IgE leader sequence SEQ ID NO:10 at the N-terminal end of the consensus immunogen sequence. The IgE leader sequence is SEQ ID NO:10 and can be encoded by SEQ ID NO:9.

There are compositions comprising an amino acid sequence that is selected from SEQ ID NO:2; SEQ ID NO:4, SEQ ID NO:6, SEQ ID NO:8; SEQ ID NO:18; SEQ ID NO:20; SEQ ID NO:22; SEQ ID NO:24; SEQ ID NO:25; or SEQ ID NO:26; or fragments thereof having at least 95% homology; or combinations thereof. In some embodiments, the compositions comprise SEQ ID NO:2; SEQ ID NO:4; SEQ ID NO:6, SEQ ID NO:8; SEQ ID NO:18; SEQ ID NO:20; SEQ ID NO:22; and SEQ ID NO:24. In some embodiments, the compositions comprise SEQ ID NO:6, SEQ ID NO:8; SEQ ID NO:18; SEQ ID NO:20; SEQ ID NO:22; and SEQ ID NO:24. In some embodiments, the compositions comprise SEQ ID NO:2; SEQ ID NO:4; SEQ ID NO:22; and SEQ ID NO:24. In some embodiments, the compositions comprise SEQ ID NO:18; SEQ ID NO:20; and SEQ ID NO:22.

The amino acid sequence can be fragments that have at least 95% homology with any one of the amino acid sequence. In some embodiments, the amino acid sequence can be fragments that have at least 98% homology with any one of the amino acid sequence. In some embodiments, the amino acid sequence can be fragments that have at least 99% homology with any one of the amino acid sequence.

According to some embodiments, methods of inducing an immune response in individuals against an immunogen comprise administering to the individual the amino acid sequence for a consensus immunogen selected from the group consisting of HPV 6 E6 and E7, HPV 11 E6 and E7, HPV 16 E6 and E7, HPV 18 E6 and E7, HPV 31 E6 and E7, HPV 33 E6 and E7, HPV 52 E6 and E7, HPV 58 E6 and E7, HPV 45 E6 and E7, and HPV 39 E6 and E7, functional fragments thereof, and expressible coding sequences thereof. Preferably, the immunogens are consensus HPV6, HPV11, HPV16, HPV18, HPV31, HPV33, HPV52, and HPV58. Preferably, the immunogens are consensus HPV16, HPV18, HPV31, HPV33, HPV52, and HPV58. Preferably, the immunogens are consensus HPV6, HPV11, HPV16, and HPV18. Preferably, the immunogens are consensus HPV16, HPV31, and HPV52.

Some embodiments comprise an isolated nucleic acid molecule that encodes the amino acid sequence for a consensus immunogen selected from the group consisting of HPV 6 E6 and E7, HPV 11 E6 and E7, HPV 16 E6 and E7, HPV 18 E6 and E7, HPV 31 E6 and E7, HPV 33 E6 and E7, HPV 52 E6 and E7, HPV 58 E6 and E7, HPV 45 E6 and E7, and HPV 39 E6 and E7, and fragments thereof. Some embodiments comprise a recombinant vaccine that encodes the amino acid sequence for a consensus immunogen selected from the group consisting of HPV 6 E6 and E7, HPV 11 E6 and E7, HPV 16 E6 and E7, HPV 18 E6 and E7, HPV 31 E6 and E7, HPV 33 E6 and E7, HPV 52 E6 and E7, HPV 58 E6 and E7, HPV 45 E6 and E7, and HPV 39 E6 and E7, and fragments thereof. Some embodiments comprise a subunit vaccine that comprises the amino acid sequence for a consensus immunogen selected from the group consisting of HPV 6 E6 and E7, HPV 11 E6 and E7, HPV 16 E6 and E7, HPV 18 E6 and E7, HPV 31 E6 and E7, HPV 33 E6 and E7, HPV 52 E6 and E7, HPV 58 E6 and E7, HPV 45 E6 and E7, and HPV 39 E6 and E7, and fragments thereof. Some embodiments comprise a live attenuated vaccine and/or a killed vaccine that comprise the amino acid sequence for a consensus immunogen selected from the group consisting of HPV 6 E6 and E7, HPV 11 E6 and E7, HPV 16 E6 and E7, HPV 18 E6 and E7, HPV 31 E6 and E7, HPV 33 E6 and E7, HPV 52 E6 and E7, HPV 58 E6 and E7, HPV 45 E6 and E7, and HPV 39 E6 and E7.

There are methods of inducing an immune response in an individual against HPV comprising administering to said individual a composition comprising a nucleic acid sequences provided herein. In some embodiments, the methods also include introducing the nucleic acid sequences into the individual by electroporation.

In some aspects, there are methods of inducing an immune response in an individual against HPV comprising administering to said individual a composition comprising a amino acid sequence provided herein. In some embodiments, the methods also include introducing the amino acid sequences into the individual by electroporation.

In one aspect, the vaccines herein are those that elicit an immune response against HPV subtypes found predominantly to be associated with forms of head and neck cancer, and other forms of otolaryngologic diseases, in particular the vaccines include HPV 6 E6 and E7 and HPV 11 E6 and E7, and preferably both.

In another aspect, the vaccines herein are those the elicit an immune response against HPV subtypes found predominantly to be associated with forms of cervical cancer in patients ex-United States and more particularly patients in Asia, in particular the vaccines include HPV 33 E6 and E7 and HPV 58 E6 and E7, and preferably both.

There are preferred combinations useful to elicit an immune response against HPV subtypes found to be associated with cervical cancer, including precancerous lesions, which include: HPV subtypes 16, 18, 31, 33, 52, 58, 6, 11, 39, and 45 or HPV subtypes 16, 18, 31, 33, 52, 58, 6, and 11. Other subcombinations for this cervical cancer include:

16 and 18; 16, 18, and 6; 16, 18, and 11; 16, 18, and 31; 16, 18, and 33; 16, 18, and 52; 16, 18, and 58; 16, 18, 6, and 11; 16, 18, 6, and 31; 16, 18, 6, and 33; 16, 18, 6, and 52, 16, 18, 6, and 58; 16, 18, 11 and 31; 16, 18, 11 and 33, 16, 18, 11 and 52; 16, 18, 11 and 58; 16, 18, 31 and 33; 16, 18, 31 and 52; 16, 18, 31 and 58; 16, 18, 33 and 52; 16, 18, 33 and 58; 16, 18, 52 and 58;

6, 11, and 16; 6, 11, and 18; 6, 11, and 31; 6, 11, and 33; 6, 11, and 52; 6, 11, and 58; 6, 11, 16, and 31; 6, 11, 16, and 33; 6, 11, 16, and 52; 6, 11, 16, and 58; 6, 11, 18, and 31; 6, 11, 18, and 33; 6, 11, 18, and 52; 6, 11, 18, and 58; 6, 11, 31, and 33; 6, 11, 31, and 52; 6, 11, 31, and 58; 6, 11, 33, and 52; 6, 11, 33, and 58; 6, 11, 52, and 58;

6, 16, and 31; 6, 16, and 33; 6, 16, and 52; 6, 16, and 58; 6, 16, 31 and 33; 6, 16, 31 and 52; 6, 16, 31 and 58; 6, 16, 33 and 52; 6, 16, 33 and 58; 6, 16, 52 and 58;

6, 18 and 31; 6, 18 and 33; 6, 18 and 52; 6, 18 and 58; 6, 18, 31 and 33; 6, 18, 31 and 52; 6, 18, 31 and 58; 6, 18, 33 and 52; 6, 18, 33 and 58;

6, 31 and 33; 6, 31 and 52; 6, 31 and 58; 6, 31, 33 and 52; 6, 31, 33 and 58;

6, 33, and 52; 6, 33, and 58; 6, 33, 52 and 58;

6, 52 and 58;

11, 31 and 33; 11, 31 and 52; 11, 31 and 58; 11, 31, 33 and 52; 11, 31, 33 and 58; 11, 31, 52 and 58;

11, 31 and 52; 11, 31 and 58; 11, 31, 52 and 58;

11, 52, and 58;

16 and 33; 16, 31, and 52; 16, 31, and 58; 16, 31, 33, and 52; 16, 31, 52, and 58;

16, 33, and 52; 16, 33, and 58; 16, 33, 52 and 58;

18, 31, and 33; 18, 31, and 52; 18, 31, and 58; 18, 31, 33 and 52; 18, 31, 33 and 58;

31, 33 and 52; 31, 33 and 58; 31, 33, 52 and 58; and 31, 52, and 58.

Improved vaccines comprise proteins and genetic constructs that encode proteins with epitopes that make them particularly effective as immunogens against which anti-HPV immune responses can be induced. Accordingly, vaccines can be provided to induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize an individual.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

The present invention relates to improved attenuated live vaccines, improved killed vaccines and improved vaccines that use recombinant vectors to deliver foreign genes that encode antigens and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,3 64; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

When taken up by a cell, the genetic construct(s) may remain present in the cell as a. functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode protein of the invention, and, additionally, genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

Examples of electroporation devices and electroporation methods preferred for facilitating delivery of the DNA vaccines, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the improved HPV vaccine is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as a-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses are provided. The vaccine may be a protein based, live attenuated vaccine, a cell vaccine, a recombinant vaccine or a nucleic acid or DNA vaccine. In some embodiments, methods of inducing an immune response in individuals against an immunogen, including methods of inducing mucosal immune responses, comprise administering to the individual one or more of CTACK protein, TECK protein, MEC protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine. The one or more of CTACK protein, TECK protein, MEC protein and functional fragments thereof may be administered prior to, simultaneously with or after administration of the isolated nucleic acid molecule that encodes an immunogen; and/or recombinant vaccine that encodes an immunogen and/or subunit vaccine that comprises an immunogen and/or live attenuated vaccine and/or killed vaccine. In some embodiments, an isolated nucleic acid molecule that encodes one or more proteins of selected from the group consisting of:

CTACK, TECK, MEC and functional fragments thereof is administered to the individual.

The present invention is further illustrated in the following Example. It should be understood that this Example, while indicating embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Each of the U.S. Patents, U.S. Applications, and references cited throughout this disclosure are hereby incorporated in their entirety by reference.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Novel Engineered HPV-16 DNA Vaccine Encoding a E6/E7 Fusion Protein

The immunogen has been designed to be expressed as a polyprotein whereby E6 and E7 sequences are separated by a proteolytic cleavage site. The polyprotein is also expressed with an IgE leader sequence. The polyprotein design includes deletions or mutations in the E6 sequence which are important for p53 binding and degradation and mutations in ribosome binding site on the E7 protein.

Coding sequences of HPV16 E6/E7 (SEQ ID NO: 21) encoding the polyprotein (SEQ ID NO:22) were inserted into the vector pVAX to generate an expression plasmid. The optimized human papilloma virus 16-6&7 antigens (HPV16 E6&7), driven by the CMV promoter (PCMV) with the bovine growth hormone 3' end and poly-adenylation signal (bGHpA) using a pVAX backbone that includes—the kanamycin resistance gene (Kan) and plasmid origin of replication (pUC ori).

HPV18 E6/E7 Vaccine Design and Expression

An optimized consensus sequences for human papilloma virus (HPV) viral proteins 18 E6&7 was prepared. The sequence is designed for high levels of expression. This sequence is useful in our genetic immunization technology. Results from experiments performed using the consensus sequence were positive. The plasmid construct includes the nucleic acid sequence of the consensus HPV 18-6&7 (SEQ ID NO: 23). The nucleic acid sequence of the consensus HPV 18-6&7 that is incorporated into the plasmid includes coding sequence for the IgE leader peptide linked to the coding sequences of the consensus HPV 18-6&7.

A expression plasmid pGX3002 was generated that expresses the optimized human papilloma virus 18-6&7 antigens (HPVI8 E6&7) (SEQ ID NO:24), driven by the CMV promoter (PCMV) with the bovine growth hormone 3' end and poly-adenylation signal (bGHpA) using a pVAX backbone that includes—the kanamycin resistance gene (Kan) and plasmid origin of replication (pUC ori).

HPV6 and HPV11 E6/E7 Vaccine Design and Expression Construction of HPV6 and 11 E6/E7 Consensus-Based Fusion Immunogens The HPV type 6 or 11 E6 and E7 gene sequences were collected from GeneBank, and the consensus E6 and E7 nucleotide sequences were obtained after performing multiple alignment. The consensus sequence of HPV 6 E6 or E7 proteins was generated from 98 or 20 sequences, respectively, while the consensus sequence of HPV 11 E6 or E7 proteins was generated from 76 or 13 sequences, respectively. The multiple alignment procedure applied in the phylogenetic study included the application of Clustal X (version 2.0). As indicated in FIG. 1A and FIG. 1B, there were about 0-2% of sequence divergence among the HPV strains belonging to the same type in their E6 and E7 proteins. However, the genetic distances could go up to 19.3% in the E6 protein and 16.3% in the E7 protein between HPV 6 and 11. Based on these results from the phylogenic analyses, we developed two type-specific E6/E7 consensus DNA vaccines.

Several modifications were conducted after generating the consensus E6/E7 fusion sequence (FIG. 1C). A highly efficient leader sequence was fused in frame upstream of the start codon to facilitate the expression. The codon and RNA optimization was also performed as described previously (J. Yan, et al., Cellular immunity induced by a novel HPV18 DNA vaccine encoding an E6/E7 fusion consensus protein in mice and rhesus macaques, Vaccine. 26 (2008) 5210-5215; and J. Yan, et al., Induction of antitumor immunity in vivo following delivery of a novel HPV-16 DNA vaccine encoding an E6/E7 fusion antigen, Vaccine. 27 (2009) 431-440). An endoproteolytic cleavage site was introduced between E6 and E7 protein for proper protein folding and better CTL processing. Both synthetic engineered 6E6E7 gene and 11E6E7 genes were 840 bp in length. The sequence verified synthetic genes were subcloned into the pVAX expression vector at the BamHI and XhoI sites respectively for further study. The consensus amino acid sequences were obtained by translating the consensus nucleotide sequences.

After obtaining HPV 6 and 11 consensus E6 and E7 sequences, condon optimization and RNA optimization was performed as previously described (J. Yan, et al., Vaccine. 26 (2008) 5210-5215; and J. Yan, et al., Induction, Vaccine. 27 (2009) 431-440). The fusion genes encoding either HPV type 6 or 11 consensus E6/E7 fusion protein (6E6E7 or 11E6E7) were synthesized and sequence verified. The synthesized 6E6E7 or 11E6E7 was digested with BamHI and XhoI, cloned into the expression vector pVAX (Invitrogen) under the control of the cytomegalovirus immediate-early promoter and these constructs were named as p6E6E7 or p11E6E7.

293-T cells were cultured in 6-well plates and transfected with pVAX, p6E6E7, or p11E6E7 using FuGENE6 Transfection Reagent (Roche Applied Science, Indianapolis, Ind.). Two days after transfection, the cells were lysed using Modified RIPA Cell Lysis Buffer and cell lysate was collected. The Western blot analyses were performed with an anti-HA monoclonal antibody (Sigma-Aldrich, St. Louis, Mo.) and visualized with horseradish peroxidase-conjugated goat anti-mouse IgG (Sigma-Aldrich, St Louis, Mo.) using an ECL™ Western blot analysis system (Amersham, Piscataway, N.J.).

Indirect immunofluorescent assays were performed using human rhabdomyosarcoma cells (RD cells) to verify expression of p6E6E7 and p11E6E7. RD cells cultured in chamber slides were transfected with pVAX, p6E6E7, or p11E6E7 using Turbofectin 8.0 (Origene, Rockville, Md.). Afterwards, the cells were fixed with PFA and permeabilized with 0.1% Triton-X in PBS. The cells were subjected to 1-2 hour incubations with primary and secondary antibodies in addition to washes of PBS supplemented with Glycine and BSA in between incubations. The primary and secondary antibodies used were monoclonal mouse anti-HA (Sigma-Aldrich, St. Louis, Mo.) and FITC-conjugated anti-mouse IgG (Abcam, Cambridge, Mass.), respectively. Hoechst staining was also performed to identify cell nuclei and localize the RD cells. After all incubations were completed, the cells were mounted with a glass slide fixed with Fluoromount-G (Southern Biotech, Birmingham, Ala.). The samples were viewed and imaged using a confocal microscope (CDB Microscopy Core, University of Pennsylvania Cell and Developmental Biology, Philadelphia, Pa.).

HPV 31, 33, 39, 45, 52 and 58 E6E7 Antigens

The HPV type 31, 33, 39, 45, 52, and 58 E6 and E7 gene sequences, individually, were collected from GeneBank, and the consensus E6 and E7 nucleotide sequences were obtained after performing multiple alignment (type31—SEQ ID NO: 18; type33—SEQ ID NO:6; type52—SEQ ID NO:20; and type58—SEQ ID NO:8). The multiple alignment procedure applied in the phylogenetic study included the application of Clustal X (version 2.0). Based on the results from the phylogenic analyses, we developed type-specific E6/E7 consensus DNA vaccines.

Several modifications were conducted after generating the consensus E6/E7 fusion sequence. A highly efficient leader sequence was fused in frame upstream of the start codon to facilitate the expression. The codon and RNA optimization was also performed as described previously (J. Yan, et al., Cellular immunity induced by a novel HPV18 DNA vaccine encoding an E6/E7 fusion consensus protein in mice and rhesus macaques, *Vaccine*. 26 (2008) 5210-5215; and J. Yan, et al., Induction of antitumor immunity in vivo following delivery of a novel HPV-16 DNA vaccine encoding an E6/E7 fusion antigen, *Vaccine*. 27 (2009) 431-440). An endoproteolytic cleavage site was introduced between E6 and E7 protein for proper protein folding and better CTL processing. The sequence verified synthetic genes were subcloned into the pVAX expression vector at the BamHI and XhoI sites respectively for further study. The consensus amino acid sequences were obtained by translating the consensus nucleotide sequences.

An expression plasmid was generated that expresses the optimized human papilloma virus 31, 33, 52, and 58-E6&7 antigens (HPV31 E6&7—SEQ ID NO:17, HPV33 E6&7—SEQ ID NO:5, HPV52 E6&7—SEQ ID NO:19, and HPV58 E6&7—SEQ ID NO:7), driven by the CMV promoter (PCMV) with the bovine growth hormone 3' end and polyadenylation signal (bGHpA) using a pVAX backbone that includes—the kanamycin resistance gene (Kan) and plasmid origin of replication (pUC ori). Likewise, an expression plasmid is generated including an insert that is the optimized human papilloma virus 39 and 45 E6&E7 antigens (HPV39 E6&E7 sequence that encodes SEQ ID NO:26; and HPV45 E6&E7 sequence that encodes SEQ ID NO:25).

Example 2

Mice and Treatment Groups Vaccinations

Female C57BL/6 mice between 6 to 8 weeks old were used in this experiment. Mice were obtained from the Jackson Laboratory (Bar Harbor, Me.). The mice were housed and maintained by the University Laboratory Animal Resources at the University of Pennsylvania (Philadelphia, Pa.) in observance with the policies of the National Institutes of Health and the University of Pennsylvania Institutional Animal Care and Use Committee (IACUC). The mice used in these experiments were separated into groups of four for immunization. Mice were immunized with p6E6E7, p11E6E7, or both constructs and pVAX group served as negative control.

DNA Vaccination and Electroporation

Each mouse received three doses of 20 µg of each DNA plasmid at 14-day intervals. Mice in the group receiving both p6E6E7 and p11E6E7 received 20 µg of both plasmids for a total of 40 µg of DNA per vaccination. The DNA constructs were administered via intramuscular injection of the right quadriceps muscle, followed by square-wave pulses generated by the CELLECTRA™ electroporator (Inovio Pharmaceuticals, Blue Bell, Pa.). The electroporator was configured to deliver two electric pulses at 0.2 Amps at 52 ms/pulse spaced apart by a 1 second delay. Electroporation procedure was performed as described previously [12, 13].

IFN-γ ELISpot Assay

Mice in both treatment and control groups were sacrificed 1 week after the third immunization. Spleens were harvested from each mouse and transferred to RPMI-1640 medium with 10% FBS and antibiotics (R10). Using a stomacher (Seward Laboratory Systems, Bohemia, N.Y.), the spleens were pulverized and subsequently transferred through a cell strainer and suspended in ACK lysing buffer. After removing erythrocytes, the splenocytes were isolated and suspended in R10 medium. High-protein IP 96-well Multiscreen™ plates (Millipore, Bedford, Mass.) were pre-coated with monoclonal mouse IFN-γ Capture Antibody (R&D Systems, Minneapolis, Minn.) and incubated overnight at 4° C. After three washes with 1×PBS, the plates were blocked with 1% BSA and 5% sucrose in 1× PBS for 2 hours at ambient temperature. Isolated splenocytes in R10 medium were counted and added in triplicate wells at 2×105 cells per well. Two sets of peptides spanning the consensus E6/E7 sequence for HPV6 and HPV11 were reconstituted in DMSO (GenScript USA, Piscataway, N.J.). The peptides contained 15 amino acid sequences, of which 8 residues overlapped with each sequential peptide. The peptides for HPV6 and 11 were each divided into two pools—one pool for E6 and another for E7—at concentrations of 2 µg/mL in DMSO. Wells reserved for positive and negative control received Concavalin A (Sigma-Aldrich, St. Louis, Mo.) and R10 culture medium in lieu of peptides, respectively. Plates were subsequently placed in a 5% CO2 atmosphere incubator. After incubation for 24 hours at 37° C., the wells were washed with 1×PBS. Biotinylated anti-mouse IFN-γ Detection Antibody (R&D Systems, Minneapolis, Minn.) was added to each well and then incubated overnight at 4° C. The plates were subsequently washed and processed per a color development protocol provided by R&D Systems using Streptavidin-AP and BCIP/NBT Plus (R&D Systems, Minneapolis, Minn.). The wells were air-dried overnight and spots inside wells were scanned and counted by an ELISpot plate reader system with ImmunoSpot® 3 and ImmunoSpot® 4 software (Cellular Technology Ltd., Shaker Heights, Ohio). Reported spot-forming cell counts were converted to represent spot-forming units per 1×106 splenocytes using arithmetic.

Given their sensitivity and ability to illustrate T-cell activity, IFN-γ ELISpot assays were used to determine the number of antigen-specific IFN-gamma secreting cells in response to stimulation with either HPV 6 or 11 E6 and E7 peptides.

As shown in FIG. 3A and FIG. 3B, the average number of SFU/106 splenocytes for mice vaccinated with p6E6E7 was 1442.8, while the average number of SFU/106 for mice immunized with p11E6E7 was 2845, which were all significantly greater than the negative control group. Therefore, both p6E6E7 and p11E6E7 were effective in eliciting robust type-specific E6 and E7-specific immune response in mice.

Interestingly, the cross-reactive cellular immune responses were also induced by vaccination with p6E6E7 or p11E6E7. The additive frequency of SFU/106 splenocytes in p11E6E7 immunized mice against HPV 6 E6/E7 peptides was 552.8 SFU/106 splenocytes, and the HPV 11 E6/E7-specific immune responses in p6E6E7 immunized mice was 888.3 SFU/106 splenocytes. The E6 proteins of HPV 6 or 11 share about 80% identity, while the E7 proteins of HPV6 or 11 shared about 84% identity. There may be some shared immune epitopes between HPV 6 or 11 E6 and E7 antigens. The cross-reactivity observed from the IFN-gamma ELISpot assay indicated that there were shared immune epitopes between HPV6 and 11 E6 and E7 antigens.

Splenocytes from mice that received both p6E6E7 and p11E6E7 (combo group) were also subjected to the above ELISpot assays in order to examine whether there was any immune interference when these two constructs were vaccinated together (FIG. 3A and FIG. 3B). The combo group exhibited an average of 1670 SFU/106 splenocytes ($\sigma$=55.7, p<0.001) against HPV6 E6 and E7 peptides. The same group of splenocytes produced 2010 SFU/106 splenocytes ($\tau$=247.8, p=0.002) against HPV11 E6 and E7 peptides. The data suggest that concurrent vaccination with the two constructs can elicit a statistically significant E6 and E7-specific cellular response against HPV6 and HPV11 and that these responses do not interfere with each other.

Epitope Mapping

Figure 4B:
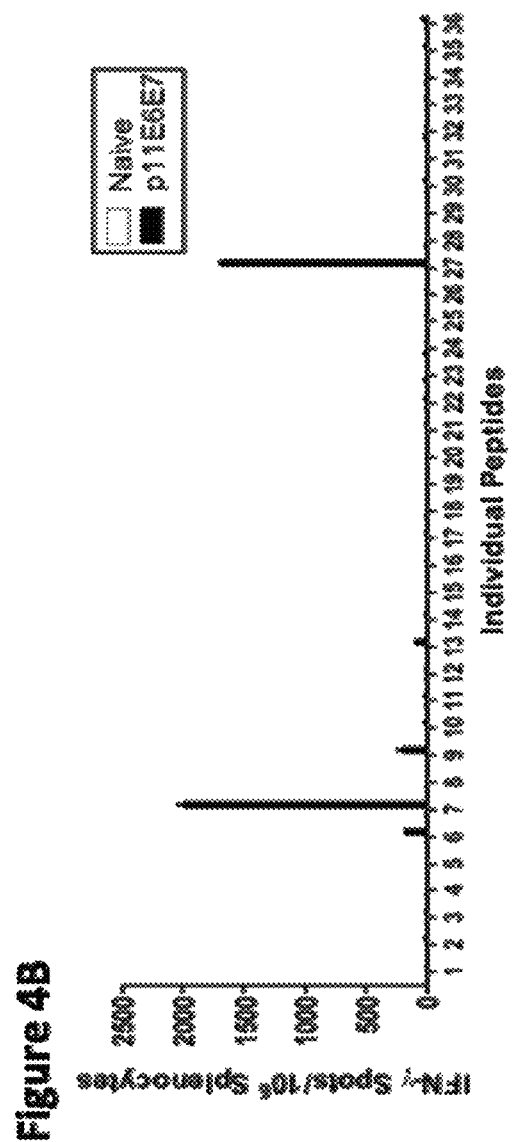

Epitope mapping studies were performed to determine dominant epitopes within peptide pools, in order to determine the immune dominant peptides within the E6/E7 consensus antigens (FIG. 4A and FIG. 4B). The studies were performed similarly to the previously mentioned IFN-$\gamma$ ELISpot assay. Instead of pools, individual peptides were used to stimulate the splenocytes.

Each peptide used in this single-peptide analysis represented a partially overlapping fragment of the E6 and E7 antigens of HPV6 or HPV11. The mapping data indicated that peptide 7 (TAEIYSYAYKQLKVL) SEQ ID NO:11 was the dominant epitope for the HPV6 E6 and E7 immunogens (FIG. 4A). TAEIYSYAYKQLKVL SEQ ID NO:11 contained 8, 9, 10-mer amino acid epitopes that are verified to be an H2-Kb restricted by the HLA-binding prediction software made available by NIH BIMAS. To further describe the HPV11 E6 and E7-specific T-cell immune response (FIG. 4B). Peptide analysis was also performed with overlapping fragments of HPV11 E6 and E7. Epitope mapping showed that the dominant epitopes for HPV 11 E6 and E7 antigens were peptides 7 (TAEIYAYAYKNLKVV) SEQ ID NO:12 and 27 (HCYEQLEDSSEDEVD) SEQ ID NO:13. As with peptide 7 in the HPV6 epitope mapping assay, the BIMAS HLA-binding prediction software confirmed TAEIYAYAYKNLKVV SEQ ID NO:12 to be an H2-Kb restricted epitope. Another HLA-binding peptide database, the Immune Epitope Database and Analysis Resource provided by NIH NIAID, confirmed that HCYEQLEDSSEDEVD SEQ ID NO:13 is an H2-Kb restricted epitope. Three immune subdominant peptides, numbers 6 (FCKNALTTAEIYSYA) SEQ ID NO:14, 9 (LFRGGYPYAACACCL) SEQ ID NO:15, and 13 (YAG-YATTVEEETKQD) SEQ ID NO:16, were identified through this epitope mapping study.

Intracellular Cytokine Staining

In light of the high immune response portrayed by the IFN-$\gamma$ ELISpot assays, intracellular cytokine staining assays were performed to provide a more holistic overview of the cellular response induced by p6E6E7 and p11E6E7. Splenocytes from vaccinated and naive mouse groups were isolated and stimulated with peptides spanning the E6 and E7 regions of HPV6 and HPV11 for 4 hours at 37° C. in a 5% CO2 environment. Positive and negative controls were used in the assay by placing cells in phorbol 12-myristate 13-acetate (PMA) and R10 cell media, respectively. After incubation, the cells were first stained with ViViD Dye (Invitrogen, Carlsbad, Calif.) to differentiate between live and dead cells, then all cells were stained with the following surface marker antibodies: APC-Cy7 Hamster anti-Mouse CD3e, PerCP-Cy5.5 Rat anti-Mouse CD4, and APC Rat anti-Mouse CD8a (BD Biosciences, San Diego, Calif.). The cells were subsequently fixed using the Cytofix/Cytoperm kit (BD Biosciences, San Diego, Calif.). After fixation per manufacturer protocol, the cells were stained with the following intracellular marker antibodies: Alexa Fluor 700 Rat anti-Mouse IFN-$\gamma$, PE-Cy7 Rat anti-Mouse TNF Clone, and PE Rat anti-Mouse IL-2 (BD Biosciences, San Diego, Calif.). After staining, the cells were fixed with a solution of PBS containing 2% paraformaldehyde. The prepared cells were acquired using an LSR II flow cytometer equipped with BD FACSDiva software (BD Biosciences, San Jose, Calif.). Acquired data was analyzed using the latest version of FlowJo software (Tree Star, Ashland, Oreg.). CD4+ and CD8+ events were isolated using the following sequence of gates: singlet from FSC-A vs FSC-H, all splenocytes from FSC-A vs SSC-A, live cells from ViViD Dye (Pacific Blue) vs SSC-A, CD3+ cells from CD3 (APC-Cy7) vs SSC-A, and CD4+ or CD8+ from CD4 (PerCP-Cy5.5: positive—CD4+, negative—CD8+) vs SSC-A. The last two populations were gated against Alexa Fluor 700, PE-Cy7, and PE to observe changes in IL-2, IFN-$\gamma$, and TNF-$\alpha$ production, respectively.

Figure 5A:
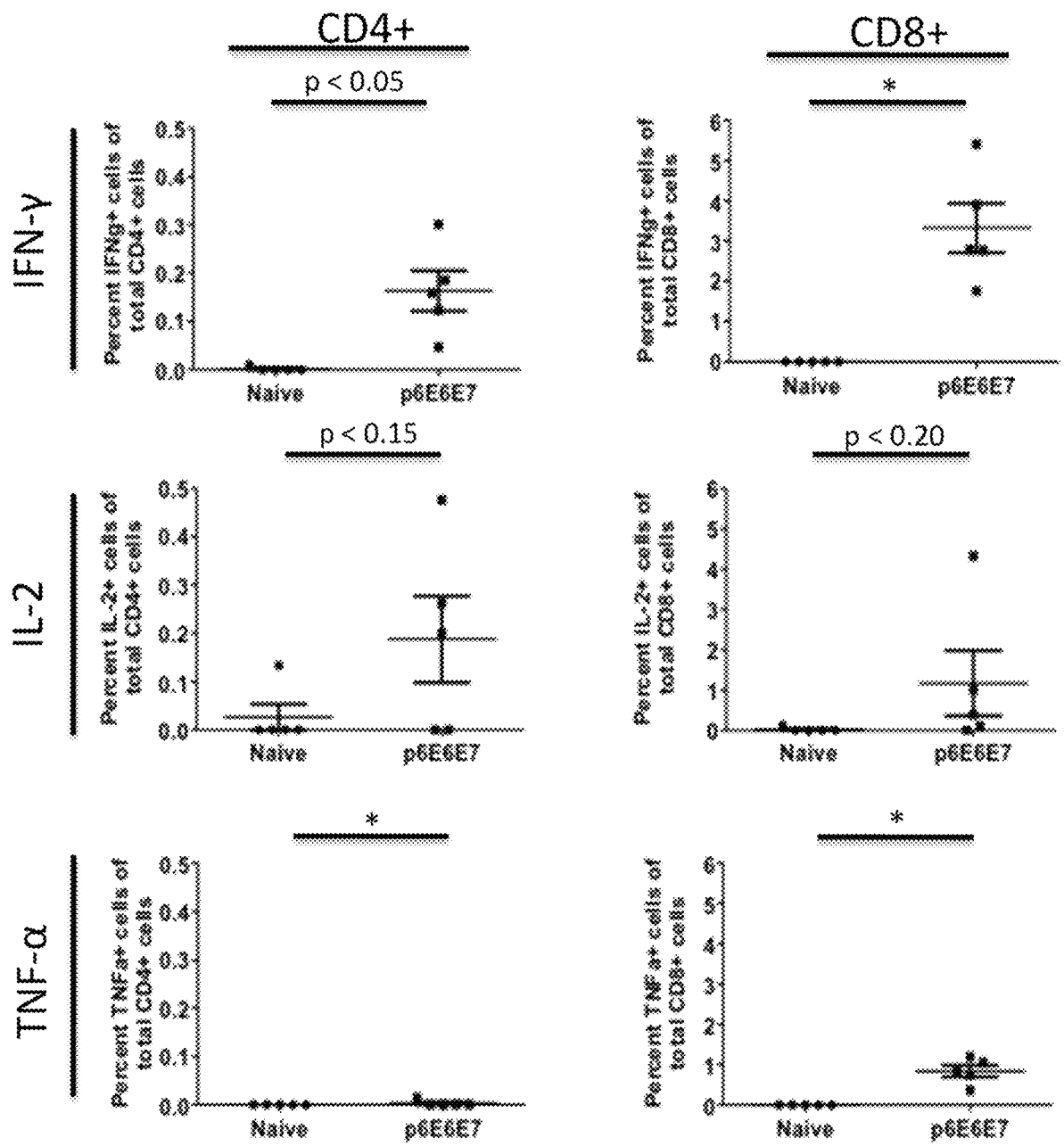
FIG. 5A through FIG. 5B depicts cytokine production by antigen-specific T-cells characterized by intracellular cytokine staining. Splenocytes isolated from mice vaccinated with p6E6E7 (FIG. 5A) and p11E6E7 (FIG. 5B) were stimulated with R10 growth medium, PMA, or consensus gene peptides for 4 hours prior to surface marker and intracellular staining. Dot plots above show differences in background-subtracted percentages of either total CD4+ or CD8+ cells producing IFN-γ, IL-2, and TNF-α. P-values for plots with asterisks were unable to be determined because the average of the negative control group was zero.
Figure 5B:
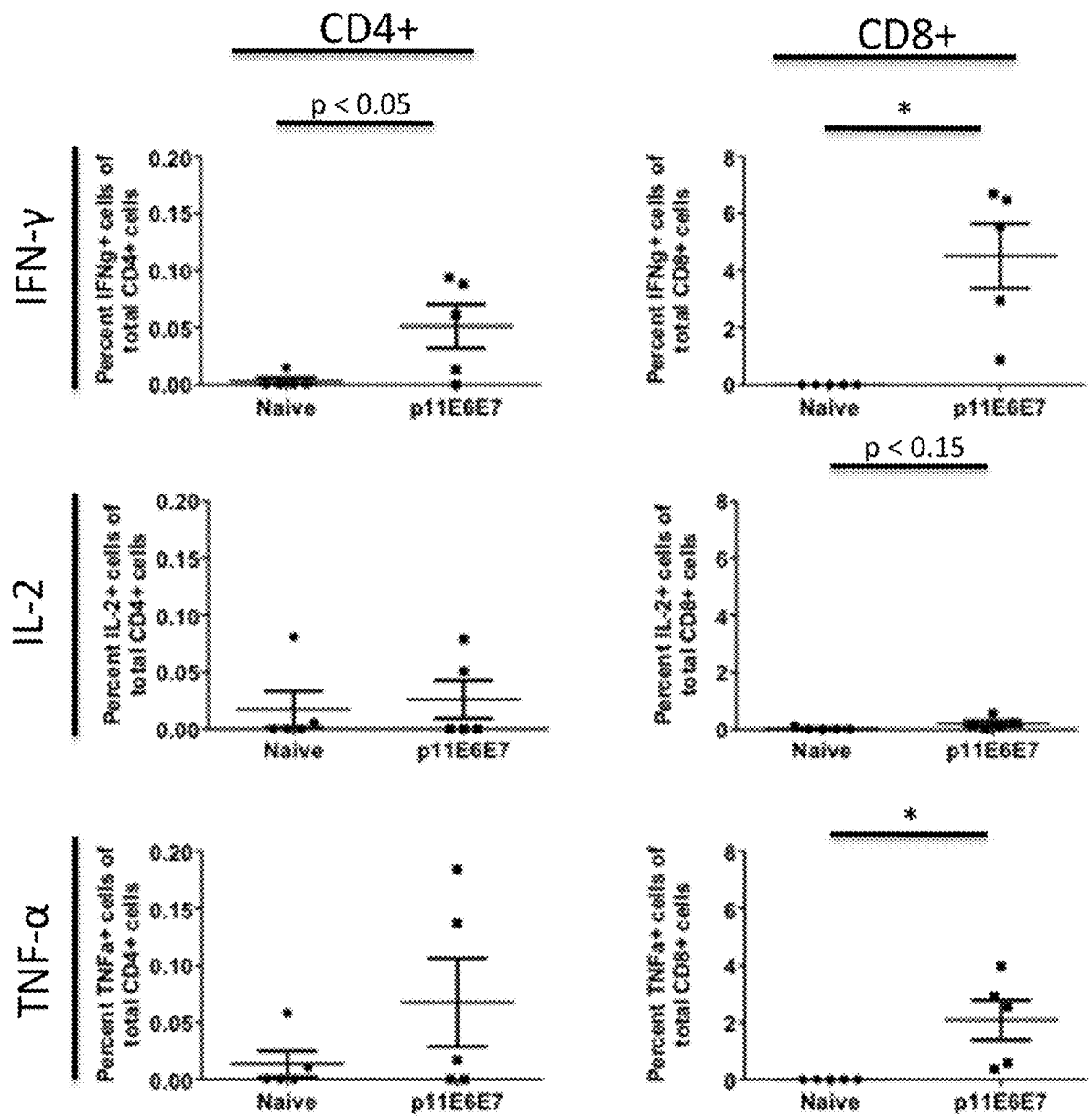

Cells were gated such that intracellular cytokine staining data can differentiate by CD4+ and CD8+ cell responses. When stimulated with HPV6 E6 and E7-specific peptides, mice vaccinated with p6E6E7 exhibited averages of 0.163% ($\sigma$=0.09), 0.003% ($\sigma$=0.07), and 0.188% ($\sigma$=0.20) of total CD4+ cells producing IFN-$\gamma$, TNF-$\alpha$, and IL-2, respectively (FIG. 5A). The same group of mice had averages of 3.323% ($\sigma$=1.39), 0.838% ($\sigma$=0.32), and 1.172% ($\sigma$=1.81) of total CD8+ cells producing IFN-$\gamma$, TNF-$\alpha$, and IL-2, respectively. The same intracellular cytokine data was collected using splenocytes from mice vaccinated with p11E6E7 after incubation with HPV11 E6 and E7 antigens (FIG. 5B). Of all CD4+ cells in the p11E6E7 vaccinated mice, an average of 0.051% ($\sigma$=0.04) produced IFN-$\gamma$, 0.068% ($\sigma$=0.09) produced TNF-$\alpha$, and 0.026% ($\sigma$=0.037) produced IL-2. Further, an average of 4.52% ($\sigma$=2.53), 2.08% ($\sigma$=1.56), and 0.21% ($\sigma$=0.22) of all CD8+ cells in p11E6E7 vaccinated mice produced IFN-$\gamma$, TNF-$\alpha$, and IL-2, respectively. With the exception of a few panels, the percentage of cytokine producing cells in treatment versus their respective naïve groups was statistically significant at a confidence level of 89% or higher. Observation of the magnitude of cytokine production of CD4+ cells versus CD8+ T-cells, one can conclude that the immune responses elicited by p6E6E7 and p11E6E7 is heavily skewed towards driving CD8+ lymphocytes, which are associated in all models with their cell clearance.

Statistical Analysis

Student's t tests were performed to analyze statistical significance of all quantitative data produced in this study. Unless otherwise indicated, p-values were calculated to determine statistical significance at various confidence levels.

This study has shown compelling evidence that DNA vaccines may be able to attain a level of immunogenicity found in experiments using other popular and traditional vaccine platforms. High levels of cellular responses measured in other similar E6 and E7-specific HPV DNA vaccine studies were associated with data suggestive of prophylactic and therapeutic anti-tumor efficacy. Most HPV-related research and disease challenge models focus on cervical cancer. Given that HPV6 and HPV11 are not as relevant to cervical cancer as other HPV serotypes, the therapeutic efficacy of p6E6E7 and p11E6E7 cannot be fully evaluated using conventional HPV disease challenge models. It would be insightful to determine the protective and therapeutic potential of p6E6E7 and p11E6E7 when appropriate disease challenge models become available. Thus, one can only infer the immunogenic efficacy of p6E6E7 and p11E6E7 by looking at the high levels of IFN-γ and cytokine production quantified by the ELISpot assays and intracellular cytokine staining. Nonetheless, such levels were found to be significantly robust in magnitude and show promise that the two constructs would elicit substantive levels of cellular immune responses. Because HPV-related malignancies are generally secondary to concurrent infection of multiple serotypes, there is a great need to look further into the feasibility of combining vaccines targeting different serotypes of the virus. Future study looking into T-cell dynamics and vaccine competition is warranted to further characterize the effects of concurrent vaccination of the two plasmids.

Intracellular cytokine staining showed that vaccination with p6E6E7 and p11E6E7 was able to elicit a significant percentage of IFN-γ, TNF-α, and IL-2 producing T-cells. Given its currently known function in the immune system, IFN-γ has historically been used as a metric of cellular immune responses. Some of these important roles include the ability to modulate and stimulate innate and adaptive immunity. Moreover, it is widely accepted that the principle producers of IFN-γ are T-cells, making IFN-γ production an acceptable mode of measuring the cellular immunogenicity of a given vaccine post-exposure to antigens. TNF-α is another cytokine that is involved in the regulation of the immune system. Its known ability to induce apoptosis and regulate tumor proliferation makes it an important parameter to consider when characterizing post-vaccination immune responses. TNF-α production may be of further interest given the potential tumor proliferative properties of HPV6 and HPV11. IL-2 is another signaling molecule that has been observed to play a central role in the proliferation and differentiation of T-cells in the immune system. As a consequence, IL-2 is often examined in conjunction with other cytokines to gain further perspective on the magnitude and quality of a particular immune response. Given the above, the significant percentages of CD4+ and CD8+ cells producing IFN-γ, TNF-α, and IL-2 after vaccination with p6E6E7 suggests that the vaccine was successful in inducing a potent immune response. With the exception of IL-2 secreting CD4+ cells, the same trend is true for cells isolated from mice vaccinated with p11E6E7. Moreover, it is noteworthy to observe that CD8+ cells heavily drove the immune responses in vaccinated mice—a characteristic that is significant in evaluating the anti-tumor efficacy of the two plasmids.

Example 3

Mice and Treatment Groups Vaccinations

Female C57BL/6 mice between 6 to 8 weeks old can be used. Mice can be obtained from the Jackson Laboratory (Bar Harbor, Me.). The mice can be separated into groups of four for immunization. Mice can be immunized with one of the following combinations: a) plasmid encoding HPV16E6E7, plasmid encoding HPV18E6E7, plasmid encoding HPV6E6E7, plasmid encoding HPV11E6E7, plasmid encoding HPV31E6E7, plasmid encoding HPV33E6E7, plasmid encoding HPV52E6E7, and plasmid encoding HPV58E6E7; b) plasmid encoding HPV16E6E7, plasmid encoding HPV18E6E7, plasmid encoding plasmid encoding HPV31E6E7, plasmid encoding HPV33E6E7, plasmid encoding HPV52E6E7, and plasmid encoding HPV58E6E7; c) plasmid encoding HPV16E6E7, plasmid encoding HPV18E6E7, plasmid encoding HPV31E6E7, and plasmid encoding HPV33E6E7; d) plasmid encoding HPV16E6E7, plasmid encoding HPV18E6E7, plasmid encoding HPV6E6E7, and plasmid encoding HPV11E6E7; and pVAX group served as negative control.

DNA Vaccination and Electroporation

Each mouse received is given three doses of 20 μg of each DNA plasmid total at 14-day intervals. The DNA constructs are administered via intramuscular injection of the right quadriceps muscle, followed by square-wave pulses generated by the CELLECTRA electroporator (Inovio Pharmaceuticals, Blue Bell, Pa.). The electroporator is configured to deliver two electric pulses at 0.2 Amps at 52 ms/pulse spaced apart by a 1 second delay. Electroporation procedure was performed as described previously, as in CELLECTRA information courtesy of Inovio Pharmaceuticals.

IFN-γ ELISpot Assay

Mice in both treatment and control groups are sacrificed 1 week after the third immunization. Spleens are harvested from each mouse and transferred to RPMI-1640 medium with 10% FBS and antibiotics (R10). Using a stomacher (Seward Laboratory Systems, Bohemia, N.Y.), the spleens are pulverized and subsequently transferred through a cell strainer and suspended in ACK lysing buffer. After removing erythrocytes, the splenocytes are isolated and suspended in R10 medium. High-protein IP 96-well Multiscreen plates (Millipore, Bedford, Mass.) are pre-coated with monoclonal mouse IFN-γ Capture Antibody (R&D Systems, Minneapolis, Minn.) and incubated overnight at 4° C. After three washes with 1×PBS, the plates are blocked with 1% BSA and 5% sucrose in 1×PBS for 2 hours at ambient temperature. Isolated splenocytes in R10 medium are counted and added in triplicate wells at 2×105 cells per well. Two sets of peptides spanning the consensus E6/E7 sequence for each HPV plasmid are reconstituted in DMSO (GenScript USA, Piscataway, N.J.). The peptides contained 15 amino acid sequences, of which 8 residues overlapped with each sequential peptide. The peptides for each HPV plasmid were each divided into two pools—one pool for E6 and another for E7—at concentrations of 2 μg/mL in DMSO. Wells that are reserved for positive and negative control receive Concavalin A (Sigma-Aldrich, St. Louis, Mo.) and R10 culture medium in lieu of peptides, respectively. Plates are subsequently placed in a 5% CO2 atmosphere incubator. After incubation for 24 hours at 37° C., the wells are washed with 1×PBS. Biotinylated anti-mouse IFN-γ Detection Antibody (R&D Systems, Minneapolis, Minn.) is added to each well and then incubated overnight at 4° C. The plates are subsequently washed and processed per a color development protocol provided by R&D Systems using Streptavidin-AP and BCIP/NBT Plus (R&D Systems, Minneapolis, Minn.). The wells are air-dried overnight and spots inside wells are scanned and counted by an ELISpot plate reader system with ImmunoSpot® 3 and ImmunoSpot® 4 software (Cellular Technology Ltd., Shaker Heights, Ohio). Reported spot-forming cell counts are converted to represent spot-forming units per 1×106 splenocytes using arithmetic.

Given their sensitivity and ability to illustrate T-cell activity, IFN-γ ELISpot assays are used to determine the number of antigen-specific IFN-gamma secreting cells in response to stimulation with either HPV 6 or 11 E6 and E7 peptides.

Example 4

Human Results from VGX-3100 Phase 1 (Combination of HPV16 E6E7 and HPV18 E6E7)

Patients with previously treated CIN 2/3
IM delivery of VGX-3100 combination DNA vaccine using CELLECTRA® constant current EP device.
See Bagarazzi et al. Sci Transl Med 4, 155ra138 (2012), which is incorporated hereby in its entirety.

| Cohort | Number of Patient | Dose (mg) |
|---|---|---|
| 1 | 6 | 0.3 × 2 plasmids (HPV16/HPV18) |
| 2 | 6 | 1 × 2 plasmids (HPV16/HPV18) |
| 3 | 6 | 3 × 2 plasmids (HPV16/HPV18) |

Antibody Response:
Antibodies against all 4 antigens with high titers in 15/18 (83%) and Western Blot confirmation in all persist to 9 mos.
Antigen-Specific Cellular Responses to HPV16,18 E6, E7:
14/18 (78%) POS by IFN-γ ELISpot (>50 SFU/106 PBMC)
Increase w/ dose up to >2500 SFU/106 PBMC for 1 Ag, >5,670 SFU/106 PBMC for all 4 antigens
5 subjects responded to all 4 antigens
Responses persist to 9 months after primary series
4th dose boosts T cell responses up to >2 years
HLA DR+/CD38+ CD8+ T cells release Granzyme B/perforin
for cell killing

The invention claimed is:

1. A composition comprising at least one HPV E6-E7 fusion antigen, wherein the E6 and E7 antigens are consensus antigens generated from an HPV subtype selected from the group consisting of HPV39 and HPV45; wherein the at least one HPV E6-E7 fusion antigen is selected from the group consisting of:
   a peptide comprising SEQ ID NO: 25 or SEQ ID NO: 26;
   a peptide comprising a sequence that is at least 95% identical to SEQ ID NO: 25;
   a peptide comprising a sequence that is at least 95% identical to SEQ ID NO: 26;
   a peptide comprising a fragment of at least 261 amino acids of SEQ ID NO: 25;
   a peptide comprising a fragment of at least 264 amino acids of SEQ ID NO: 26;
   a peptide comprising a sequence that is at least 95% identical to a fragment of at least 261 amino acids of SEQ ID NO: 25; and
   a peptide comprising a sequence that is at least 95% identical to a fragment of at least 264 amino acids of SEQ ID NO: 26.

2. The composition of claim 1, wherein the HPV E6-E7 fusion antigen comprises a sequence at least 98% identical to a sequence selected from the group consisting of:
   SEQ ID NO:25 and SEQ ID NO:26.

3. The composition of claim 1, wherein the HPV E6-E7 fusion antigen comprises a sequence at least 99% identical to a sequence selected from the group consisting of:
   SEQ ID NO:25 and SEQ ID NO:26.

4. The composition of claim 1, where the HPV E6-E7 fusion antigen is without a leader sequence of SEQ ID NO:10.

5. A pharmaceutical composition comprising a HPV E6-E7 fusion antigen of claim 1.

6. A method of inducing an effective immune response in an individual against more than one subtype of HPV, comprising administering to said individual a composition comprising a HPV E6-E7 fusion antigen of claim 1.

* * * * *

SEQUENCE LISTING

```
<160> NUMBER OF SEQ ID NOS: 26

<210> SEQ ID NO 1
<211> LENGTH: 873
<212> TYPE: DNA
<213> ORGANISM: Artificial Sequence
<220> FEATURE:
<223> OTHER INFORMATION: HPV6 E6E7 DNA sequence

<400> SEQUENCE: 1
ggtaccggat ccgccaccat ggactggacc tggattctgt tcctggtggc cgctgccaca     60
cgggtgcaca gcgaaagcgc caatgccagc accagcgcta caaccatcga ccagctgtgc    120
aagaccttca acctgagcat gcacaccctg cagatcaact gcgtgttctg caagaacgcc    180
ctgaccaccg ccgagatcta cagctacgcc tacaagcagc tgaaggtgct gttcagaggc    240
ggctacccct atgccgcctg cgcctgctgc ctggaatttc acggcaagat caaccagtac    300
cggcacttcg actacgccgg ctacgccacc accgtggaag aggaaacaaa gcaggacatc    360
ctggacgtgc tgatccggtg ctacctgtgc cacaagcccc tgtgcgaggt ggaaaaagtg    420
aagcacatcc tgaccaaggc ccggttcatc aagctgaact gcacctggaa gggccggtgc    480
ctgcactgct ggaccacctg tatggaagat atgctgccca gaggccggaa gcggcggagc    540
catggcagac acgtgaccct gaaggacatc gtgctggacc tgcagccccc cgatcctgtg    600
ggcctgcact gttacgagca gctggtggac agcagcgagg acgaggtgga cgaagtggac    660
ggccaggaca gccagcccct gaagcagcac ttccagatcg tgacctgctg ctgcggctgc    720
gacagcaacg tgcggctggt ggtgcagtgc accgagacag acatcagaga ggtccagcag    780
ctcctgctgg gcaccctgaa catcgtgtgc cccatctgcg ccccaagac ctacccttac     840 gacgtgcccg actacgcctg atgactcgag ctc                                  873

<210> SEQ ID NO 2
<211> LENGTH: 280
<212> TYPE: PRT
<213> ORGANISM: Artificial Sequence
<220> FEATURE:
<223> OTHER INFORMATION: HPV6 E6E7 protein sequence
```

<400> SEQUENCE: 2

```
Met Asp Trp Thr Trp Ile Leu Phe Leu Val Ala Ala Ala Thr Arg Val
1               5                   10                  15

His Ser Glu Ser Ala Asn Ala Ser Thr Ser Ala Thr Thr Ile Asp Gln
            20                  25                  30

Leu Cys Lys Thr Phe Asn Leu Ser Met His Thr Leu Gln Ile Asn Cys
        35                  40                  45

Val Phe Cys Lys Asn Ala Leu Thr Thr Ala Glu Ile Tyr Ser Tyr Ala
    50                  55                  60

Tyr Lys Gln Leu Lys Val Leu Phe Arg Gly Gly Tyr Pro Tyr Ala Ala
65                  70                  75                  80

Cys Ala Cys Cys Leu Glu Phe His Gly Lys Ile Asn Gln Tyr Arg His
                85                  90                  95

Phe Asp Tyr Ala Gly Tyr Ala Thr Thr Val Glu Glu Thr Lys Gln
            100                 105                 110

Asp Ile Leu Asp Val Leu Ile Arg Cys Tyr Leu Cys His Lys Pro Leu
            115                 120                 125

Cys Glu Val Glu Lys Val Lys His Ile Leu Thr Lys Ala Arg Phe Ile
        130                 135                 140

Lys Leu Asn Cys Thr Trp Lys Gly Arg Cys Leu His Cys Trp Thr Thr
145                 150                 155                 160

Cys Met Glu Asp Met Leu Pro Arg Gly Arg Lys Arg Ser His Gly
                165                 170                 175

Arg His Val Thr Leu Lys Asp Ile Val Leu Asp Leu Gln Pro Pro Asp
            180                 185                 190

Pro Val Gly Leu His Cys Tyr Glu Gln Leu Val Asp Ser Ser Glu Asp
        195                 200                 205

Glu Val Asp Glu Val Asp Gly Gln Asp Ser Gln Pro Leu Lys Gln His
    210                 215                 220

Phe Gln Ile Val Thr Cys Cys Gly Cys Asp Ser Asn Val Arg Leu
225                 230                 235                 240

Val Val Gln Cys Thr Glu Thr Asp Ile Arg Glu Val Gln Gln Leu Leu
                245                 250                 255

Leu Gly Thr Leu Asn Ile Val Cys Pro Ile Cys Ala Pro Lys Thr Tyr
            260                 265                 270

Pro Tyr Asp Val Pro Asp Tyr Ala
        275                 280
```

<210> SEQ ID NO 3
<211> LENGTH: 873
<212> TYPE: DNA
<213> ORGANISM: Artificial Sequence
<220> FEATURE:
<223> OTHER INFORMATION: HPV11 E6E7 DNA sequence

<400> SEQUENCE: 3

```
ggtaccggat ccgccaccat ggactggacc tggattctgt tcctggtggc cgctgccaca    60
agagtgcaca gcgagagcaa ggatgccagc accagcgcca ccagcatcga ccagctgtgc   120
aagaccttca acctgagcct gcacaccctg cagatccagt gcgtgttctg ccggaacgcc   180
ctgaccaccg ccgagatcta cgcctacgcc tacaagaacc tgaaggtcgt gtggcgggac   240
aacttcccct cgccgcctg cgcctgctgc ctggaactgc agggcaagat caaccagtac   300
cggcacttca actacgccgc ttacgccccc accgtggaag aggaaacaaa cgaggacatc   360
ctgaaggtgc tgatccggtg ctacctgtgc cacaagcccc tgtgcgagat cgagaagctg   420
```

```
aagcacatcc tgggcaaggc ccggttcatc aagctgaaca accagtggaa gggccggtgc    480
ctgcactgct ggaccacctg tatggaagat ctgctgccca gaggccgaa gcggagaagc     540 cacggcagac tggtcaccct gaaggacatc gtgctggacc tgcagccccc cgatcctgtg    600
ggcctgcact gttacgagca gctggaagat agcagcgagg acgaggtgga caaagtggac    660
aagcaggacg cccagcccct gacccagcac taccagatcc tgacctgctg ctgcggctgc    720
gacagcaacg tgcggctggt ggtggaatgc accgacggcg acatccggca gctccaggat    780
ctgctgctgg gcaccctgaa catcgtgtgc cccatctgcg cccccaagcc ctaccctac    840 gacgtgcccg actacgcctg atgactcgag ctc                                 873
```

<210> SEQ ID NO 4
<211> LENGTH: 280
<212> TYPE: PRT
<213> ORGANISM: Artificial Sequence
<220> FEATURE:
<223> OTHER INFORMATION: HPV11 E6E7 protein sequence
<400> SEQUENCE: 4

```
Met Asp Trp Thr Trp Ile Leu Phe Leu Val Ala Ala Ala Thr Arg Val
1               5                   10                  15

His Ser Glu Ser Lys Asp Ala Ser Thr Ser Ala Thr Ser Ile Asp Gln
            20                  25                  30

Leu Cys Lys Thr Phe Asn Leu Ser Leu His Thr Leu Gln Ile Gln Cys
        35                  40                  45

Val Phe Cys Arg Asn Ala Leu Thr Thr Ala Glu Ile Tyr Ala Tyr Ala
    50                  55                  60

Tyr Lys Asn Leu Lys Val Val Trp Arg Asp Asn Phe Pro Phe Ala Ala
65                  70                  75                  80

Cys Ala Cys Cys Leu Glu Leu Gln Gly Lys Ile Asn Gln Tyr Arg His
                85                  90                  95

Phe Asn Tyr Ala Ala Tyr Ala Pro Thr Val Glu Glu Glu Thr Asn Glu
            100                 105                 110

Asp Ile Leu Lys Val Leu Ile Arg Cys Tyr Leu Cys His Lys Pro Leu
        115                 120                 125

Cys Glu Ile Glu Lys Leu Lys His Ile Leu Gly Lys Ala Arg Phe Ile
    130                 135                 140

Lys Leu Asn Asn Gln Trp Lys Gly Arg Cys Leu His Cys Trp Thr Thr
145                 150                 155                 160

Cys Met Glu Asp Leu Leu Pro Arg Gly Arg Lys Arg Arg Ser His Gly
                165                 170                 175

Arg Leu Val Thr Leu Lys Asp Ile Val Leu Asp Leu Gln Pro Pro Asp
            180                 185                 190

Pro Val Gly Leu His Cys Tyr Glu Gln Leu Glu Asp Ser Ser Glu Asp
        195                 200                 205

Glu Val Asp Lys Val Asp Lys Gln Asp Ala Gln Pro Leu Thr Gln His
    210                 215                 220

Tyr Gln Ile Leu Thr Cys Cys Gly Cys Asp Ser Asn Val Arg Leu
225                 230                 235                 240

Val Val Glu Cys Thr Asp Gly Asp Ile Arg Gln Leu Gln Asp Leu Leu
                245                 250                 255

Leu Gly Thr Leu Asn Ile Val Cys Pro Ile Cys Ala Pro Lys Pro Tyr
            260                 265                 270

Pro Tyr Asp Val Pro Asp Tyr Ala
        275                 280
```

<210> SEQ ID NO 5
<211> LENGTH: 828
<212> TYPE: DNA
<213> ORGANISM: Artificial Sequence
<220> FEATURE:
<223> OTHER INFORMATION: HPV33 E6E7 DNA sequence

<400> SEQUENCE: 5

```
ggtaccgtcg acggatccgc caccatggac tggacctgga ttctgttcct ggtggccgct      60
gctacccggg tgcacagctt ccaggacacc gaggaaagcg gccggaccct gcacgatctg     120
tgccaggccc tggaaaccac catccacaac atcgagctgc agtgcgtgga atgcaagaag     180
cccctgcagc ggagcgaggt gtacgacgcc gacctgaccg tggtgtacag agagggcaac     240
cccttcggca tctgcaagct gtgcctgcgg ttcctgagca agatcagcga gtaccggcac     300
tacaactaca cgtgtacgg caacaccctg aacagacctg tgaagaagcc tctgaacgag     360
atcctgatcc ggtgcatcat ctgccagcgg cccctgaagc ggcacgtgga cctgaacaag     420
cggttccaca atatcagcgg cagatgggcc ggcagatgcg ccgcctgttg gagaagccgg     480
cggagagaga cagccctgcg gggcagaaag cggcggagca gaggccacaa gcccaccctg     540
aaagaatacg tgctggacct gtaccccgag cccaccgacc tgtacggcta cggccagctg     600
agcgacagca gcgacgagga cgagggcctg gacagacctg atggacaggc ccagcccgcc     660
accgccgact actacatcgt gacctgctgc cacacctgta acaccaccgt gcggctgtgc     720
gtgaacagca ccgccagcga cctgcgggac atccagcagc tcctgatggg caccgtgaac     780
atcgtgtgcc ctacctgcgc ccagctgtga ctcgagacgc gtgagctc                 828
```

<210> SEQ ID NO 6
<211> LENGTH: 261
<212> TYPE: PRT
<213> ORGANISM: Artificial Sequence
<220> FEATURE:
<223> OTHER INFORMATION: HPV33 E6E7 protein sequence

<400> SEQUENCE: 6

```
Met Asp Trp Thr Trp Ile Leu Phe Leu Val Ala Ala Thr Arg Val
1               5                  10                  15

His Ser Phe Gln Asp Thr Glu Glu Ser Gly Arg Thr Leu His Asp Leu
            20                  25                  30

Cys Gln Ala Leu Glu Thr Thr Ile His Asn Ile Glu Leu Gln Cys Val
        35                  40                  45

Glu Cys Lys Lys Pro Leu Gln Arg Ser Glu Val Tyr Asp Ala Asp Leu
    50                  55                  60

Thr Val Val Tyr Arg Glu Gly Asn Pro Phe Gly Ile Cys Lys Leu Cys
65                  70                  75                  80

Leu Arg Phe Leu Ser Lys Ile Ser Glu Tyr Arg His Tyr Asn Tyr Ser
                85                  90                  95

Val Tyr Gly Asn Thr Leu Glu Gln Thr Val Lys Lys Pro Leu Asn Glu
            100                 105                 110

Ile Leu Ile Arg Cys Ile Ile Cys Gln Arg Pro Leu Lys Arg His Val
        115                 120                 125

Asp Leu Asn Lys Arg Phe His Asn Ile Ser Gly Arg Trp Ala Gly Arg
    130                 135                 140

Cys Ala Ala Cys Trp Arg Ser Arg Arg Glu Thr Ala Leu Arg Gly
145                 150                 155                 160

Arg Lys Arg Arg Ser Arg Gly His Lys Pro Thr Leu Lys Glu Tyr Val
                165                 170                 175
```

Leu Asp Leu Tyr Pro Glu Pro Thr Asp Leu Tyr Gly Tyr Gly Gln Leu
            180                 185                 190

Ser Asp Ser Ser Asp Glu Asp Glu Gly Leu Asp Arg Pro Asp Gly Gln
        195                 200                 205

Ala Gln Pro Ala Thr Ala Asp Tyr Tyr Ile Val Thr Cys Cys His Thr
    210                 215                 220

Cys Asn Thr Thr Val Arg Leu Cys Val Asn Ser Thr Ala Ser Asp Leu
225                 230                 235                 240

Arg Thr Ile Gln Gln Leu Leu Met Gly Thr Val Asn Ile Val Cys Pro
            245                 250                 255

Thr Cys Ala Gln Leu
        260

<210> SEQ ID NO 7
<211> LENGTH: 835
<212> TYPE: DNA
<213> ORGANISM: Artificial Sequence
<220> FEATURE:
<223> OTHER INFORMATION: HPV58 E6E7 DNA sequence

<400> SEQUENCE: 7

```
ggtaccgttt aaacggatcc gccaccatgg actggacctg gattctgttc ctggtggccg     60
ctgctacccg ggtgcacagc ttccaggatg ccgaggaaag cggccggacc ctgcacgatc    120
tgtgccaggc cctggaaacc agcgtgcacg agatcgagct gaagtgcgtg aatgcaaga    180
aaaccctgca gcggagcgag gtgtacgacg ccgacctgcg gatcgtgtac cggacggca    240
acccttcgc cgtgtgcaaa gtgtgcctgc ggctgctgag caagatcagc gagtaccggc    300
actacaacta cagcctgtac ggcgacaccc tggaacagac cctgaagaag tgcctgaacg    360
agatcctgat ccggtgcatc atctgccagc ggcccctgaa cggcacgtg acctgaaca    420
agcggttcca caacatcagc ggccggtgga ccggcagatg cgccgtgtgt ggaggcccca    480
ggcggagaca gacccaggtg cgcggcagaa agcggcggag cagaggcaac aaccccaccc    540
tgagagagta catcctggac ctgcaccccg agcccaccga cctgtttggc tacggccagc    600
tgtgcgacag cagcgacgag gacgagatcg gcctggacgg ccctgatgga caggcccagc    660
ccgccaccgc caactactac atcgtgacct gctgctacac ctgtggcacc accgtgcggc    720
tgtgcatcaa cagcaccacc accgacgtgc cacccctgca gcagctcctg atgggcacct    780
gtaccatcgt gtgccccagc tgcgcccagc agtgactcga ggcggccgcg agctc         835
```

<210> SEQ ID NO 8
<211> LENGTH: 262
<212> TYPE: PRT
<213> ORGANISM: Artificial Sequence
<220> FEATURE:
<223> OTHER INFORMATION: HPV58 E6E7 protein sequence

<400> SEQUENCE: 8

Met Asp Trp Thr Trp Ile Leu Phe Leu Val Ala Ala Ala Thr Arg Val
1               5                   10                  15

His Ser Phe Gln Asp Ala Glu Glu Ser Gly Arg Thr Leu His Asp Leu
            20                  25                  30

Cys Gln Ala Leu Glu Thr Ser Val His Glu Ile Glu Leu Lys Cys Val
        35                  40                  45

Glu Cys Lys Lys Thr Leu Gln Arg Ser Glu Val Tyr Asp Ala Asp Leu
    50                  55                  60

```
Arg Ile Val Tyr Arg Asp Gly Asn Pro Phe Ala Val Cys Lys Val Cys
 65                  70                  75                  80

Leu Arg Leu Leu Ser Lys Ile Ser Glu Tyr Arg His Tyr Asn Tyr Ser
                 85                  90                  95

Leu Tyr Gly Asp Thr Leu Glu Gln Thr Leu Lys Lys Cys Leu Asn Glu
            100                 105                 110

Ile Leu Ile Arg Cys Ile Ile Cys Gln Arg Pro Leu Lys Arg His Val
        115                 120                 125

Asp Leu Asn Lys Arg Phe His Asn Ile Ser Gly Arg Trp Thr Gly Arg
    130                 135                 140

Cys Ala Val Cys Trp Arg Pro Arg Arg Gln Thr Gln Val Arg Gly
145                 150                 155                 160

Arg Lys Arg Arg Ser Arg Gly Asn Asn Pro Thr Leu Arg Glu Tyr Ile
                165                 170                 175

Leu Asp Leu His Pro Glu Pro Thr Asp Leu Phe Gly Tyr Gly Gln Leu
            180                 185                 190

Cys Asp Ser Ser Asp Glu Asp Glu Ile Gly Leu Asp Gly Pro Asp Gly
        195                 200                 205

Gln Ala Gln Pro Ala Thr Ala Asn Tyr Tyr Ile Val Thr Cys Cys Tyr
    210                 215                 220

Thr Cys Gly Thr Thr Val Arg Leu Cys Ile Asn Ser Thr Thr Thr Asp
225                 230                 235                 240

Val Arg Thr Leu Gln Gln Leu Leu Met Gly Thr Cys Thr Ile Val Cys
                245                 250                 255

Pro Ser Cys Ala Gln Gln
            260

<210> SEQ ID NO 9
<211> LENGTH: 54
<212> TYPE: DNA
<213> ORGANISM: Artificial Sequence
<220> FEATURE:
<223> OTHER INFORMATION: IgE Leader DNA sequence

<400> SEQUENCE: 9
atggactgga cctggatcct gttcctggtg gccgctgcca cacgggtgca cagc      54

<210> SEQ ID NO 10
<211> LENGTH: 18
<212> TYPE: PRT
<213> ORGANISM: Artificial Sequence
<220> FEATURE:
<223> OTHER INFORMATION: IgE leader protein

<400> SEQUENCE: 10

Met Asp Trp Thr Trp Ile Leu Phe Leu Val Ala Ala Thr Arg Val
 1               5                  10                  15

His Ser

<210> SEQ ID NO 11
<211> LENGTH: 15
<212> TYPE: PRT
<213> ORGANISM: Artificial Sequence
<220> FEATURE:
<223> OTHER INFORMATION: HPV6 peptide 7
```

-continued

<400> SEQUENCE: 11

Thr Ala Glu Ile Tyr Ser Tyr Ala Tyr Lys Gln Leu Lys Val Leu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: HPV11 peptide 7

<400> SEQUENCE: 12

Thr Ala Glu Ile Tyr Ala Tyr Ala Tyr Lys Asn Leu Lys Val Val
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: HPV11 peptide 27

<400> SEQUENCE: 13

His Cys Tyr Glu Gln Leu Glu Asp Ser Ser Glu Asp Glu Val Asp
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: HPV subdominant peptide 6

<400> SEQUENCE: 14

Phe Cys Lys Asn Ala Leu Thr Thr Ala Glu Ile Tyr Ser Tyr Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: HPV subdominant peptide 9

<400> SEQUENCE: 15

Leu Phe Arg Gly Gly Tyr Pro Tyr Ala Ala Cys Ala Cys Cys Leu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: HPV subdominant peptide 13

<400> SEQUENCE: 16

Tyr Ala Gly Tyr Ala Thr Thr Val Glu Glu Glu Thr Lys Gln Asp
1               5                   10                  15

<210> SEQ ID NO 17
<211> LENGTH: 792
<212> TYPE: DNA
<213> ORGANISM: Artificial Sequence
<220> FEATURE:
<223> OTHER INFORMATION: pGX3005 insert HPV31 E6/E7 DNA sequence

<400> SEQUENCE: 17

```
atggactgga catggattct gttcctggtc gccgccgcaa ctagagtgca ttcattcaaa       60
aaccccgccg agtctgggag aaaactgcac gagctgagct ccgcactgga gatcccctac      120
gatgaactga gctgaactg cgtgtattgt aaaggacagc tgactgagac cgaagtgctg      180
gacactgatc tgaccattgt ctaccgagac gatacacctt atggcgtgtg cactaaatgt      240
ctgcgcttct actcaaaggt gagcgagttt agatggtaca ggtatagcgt ctatggcacc      300
acactggaaa aactgacaaa caaggggatc tgcgacctgc tgatcaggtg cattacttgt      360
cagcgccctc tgcagcgaca cctggataag aagaagcggt tccataatat cggcgggcgg      420
tggaccggga gatgcatcgt gtgctggcgg agaccacgga cagagactca ggtccgaggg      480
cggaaaaggc gctctagagg agaaacccca acactgcagg actacgtgct ggatctgcag      540
cccgaggcca cagacctgca tggatatggc cagctgcccg actctagtga tgaggaagac      600
gtgatcgata gtcccgccgg ccaggctaag cctgataacct ccaactacaa tattgtcaca      660
ttttgctgtc agtcgaatc cactctgagg ctgtgcgtgc agtctaccca ggtcgacatc      720
cgcattctgc aggaactgct gatgggatct ttcggaatcg tgtgccctaa ttgctccacc      780
agactgtgat aa                                                          792
```

<210> SEQ ID NO 18
<211> LENGTH: 262
<212> TYPE: PRT
<213> ORGANISM: Artificial Sequence
<220> FEATURE:
<223> OTHER INFORMATION: pGX3005 insert HPV31 E6/E7 protein sequence

<400> SEQUENCE: 18

```
Met Asp Trp Thr Trp Ile Leu Phe Leu Val Ala Ala Ala Thr Arg Val
1               5                   10                  15

His Ser Phe Lys Asn Pro Ala Glu Ser Gly Arg Lys Leu His Glu Leu
            20                  25                  30

Ser Ser Ala Leu Glu Ile Pro Tyr Asp Glu Leu Arg Leu Asn Cys Val
        35                  40                  45

Tyr Cys Lys Gly Gln Leu Thr Glu Thr Glu Val Leu Asp Thr Asp Leu
    50                  55                  60

Thr Ile Val Tyr Arg Asp Asp Thr Pro Tyr Gly Val Cys Thr Lys Cys
65                  70                  75                  80

Leu Arg Phe Tyr Ser Lys Val Ser Glu Phe Arg Trp Tyr Arg Tyr Ser
                85                  90                  95

Val Tyr Gly Thr Thr Leu Glu Lys Leu Thr Asn Lys Gly Ile Cys Asp
            100                 105                 110

Leu Leu Ile Arg Cys Ile Thr Cys Gln Arg Pro Leu Gln Arg His Leu
        115                 120                 125

Asp Lys Lys Lys Arg Phe His Asn Ile Gly Gly Arg Trp Thr Gly Arg
    130                 135                 140

Cys Ile Val Cys Trp Arg Arg Pro Arg Thr Glu Thr Gln Val Arg Gly
145                 150                 155                 160

Arg Lys Arg Arg Ser Arg Gly Glu Thr Pro Thr Leu Gln Asp Tyr Val
                165                 170                 175

Leu Asp Leu Gln Pro Glu Ala Thr Asp Leu His Gly Tyr Gly Gln Leu
            180                 185                 190

Pro Asp Ser Ser Asp Glu Glu Asp Val Ile Asp Ser Pro Ala Gly Gln
        195                 200                 205
```

-continued

```
Ala Lys Pro Asp Thr Ser Asn Tyr Asn Ile Val Thr Phe Cys Cys Gln
    210                 215                 220

Cys Glu Ser Thr Leu Arg Leu Cys Val Gln Ser Thr Gln Val Asp Ile
225                 230                 235                 240

Arg Ile Leu Gln Glu Leu Leu Met Gly Ser Phe Gly Ile Val Cys Pro
                245                 250                 255

Asn Cys Ser Thr Arg Leu
            260

<210> SEQ ID NO 19
<211> LENGTH: 792
<212> TYPE: DNA
<213> ORGANISM: Artificial Sequence
<220> FEATURE:
<223> OTHER INFORMATION: pGX3007 insert HPV52 E6/E7 DNA sequence

<400> SEQUENCE: 19
atggactgga cctggattct gttcctggtg gctgctgcta cacgggtgca ttcatttgaa     60
gaccctgcta catctggacg aactctgcac gagctgtgcg aagtgctgga ggaatctgtc    120
catgagatca ggctgcagtg cgtgcagtgt aagaaagagc tgcagcggag agaagtgtac    180
aagaccgacc tgcggattgt ctacagagat aacaatccct atggagtgtg catcatgtgc    240
ctgcggttcc tgtctaaaat tagtgaatac agacactacc agtattccct gtatggcaag    300
acactggagg aacgagtgcg gaaaccactg tctgagatca ccattcgctg catcatttgt    360
cagacacccc tggaacgaca cgtcaacgca acaagcggt tccataacat catgggaagg    420
tggactggcc gctgcagtga gtgttggaga ccaaggcctg tgacccaggt ccgcggacga    480
aaacggcgga gccggggcga caaggcaacc atcaaagact acattctgga tctgcagcct    540 agaccacag atctgcatgg ctatgggcag ctgggggaca gctccgatga ggaagacaca    600
gatggggtgg acagaccaga tggacaggcc gaacaggcta caagcaatta ctatatcgtc    660
acttattgcc actcatgtga cagcactctg aggctgtgca ttcattccac tgctaccgat    720
ctgcgcacac tgcagcagat gctgctggga acactgcagg tggtctgtcc aggatgtgcc    780
cgactgtgat aa                                                        792

<210> SEQ ID NO 20
<211> LENGTH: 262
<212> TYPE: PRT
<213> ORGANISM: Artificial Sequence
<220> FEATURE:
<223> OTHER INFORMATION: pGX3007 insert HPV52 E6/E7 protein sequence

<400> SEQUENCE: 20

Met Asp Trp Thr Trp Ile Leu Phe Leu Val Ala Ala Ala Thr Arg Val
1               5                   10                  15

His Ser Phe Glu Asp Pro Ala Thr Ser Gly Arg Thr Leu His Glu Leu
                20                  25                  30

Cys Glu Val Leu Glu Glu Ser Val His Glu Ile Arg Leu Gln Cys Val
            35                  40                  45

Gln Cys Lys Lys Glu Leu Gln Arg Arg Glu Val Tyr Lys Thr Asp Leu
        50                  55                  60

Arg Ile Val Tyr Arg Asp Asn Asn Pro Tyr Gly Val Cys Ile Met Cys
65                  70                  75                  80

Leu Arg Phe Leu Ser Lys Ile Ser Glu Tyr Arg His Tyr Gln Tyr Ser
                85                  90                  95
```

```
Leu Tyr Gly Lys Thr Leu Glu Glu Arg Val Arg Lys Pro Leu Ser Glu
            100                 105                 110

Ile Thr Ile Arg Cys Ile Ile Cys Gln Thr Pro Leu Glu Arg His Val
        115                 120                 125

Asn Ala Asn Lys Arg Phe His Asn Ile Met Gly Arg Trp Thr Gly Arg
    130                 135                 140

Cys Ser Glu Cys Trp Arg Pro Arg Pro Val Thr Gln Val Arg Gly Arg
145                 150                 155                 160

Lys Arg Arg Ser Arg Gly Asp Lys Ala Thr Ile Lys Asp Tyr Ile Leu
                165                 170                 175

Asp Leu Gln Pro Glu Thr Thr Asp Leu His Gly Tyr Gly Gln Leu Gly
            180                 185                 190

Asp Ser Ser Asp Glu Glu Asp Thr Asp Gly Val Asp Arg Pro Asp Gly
        195                 200                 205

Gln Ala Glu Gln Ala Thr Ser Asn Tyr Tyr Ile Val Thr Tyr Cys His
    210                 215                 220

Ser Cys Asp Ser Thr Leu Arg Leu Cys Ile His Ser Thr Ala Thr Asp
225                 230                 235                 240

Leu Arg Thr Leu Gln Gln Met Leu Leu Gly Thr Leu Gln Val Val Cys
                245                 250                 255

Pro Gly Cys Ala Arg Leu
            260

<210> SEQ ID NO 21
<211> LENGTH: 818
<212> TYPE: DNA
<213> ORGANISM: Artificial Sequence
<220> FEATURE:
<223> OTHER INFORMATION: HPV genotype 16 E6-E7 DNA sequence

<400> SEQUENCE: 21
gaattcgcca ccatggactg gacctggatc ctgttcctgg tggccgccgc cacacgggtg      60
cacagcttcc aggaccccca ggagagcggc agaaagctgc tcagctgtg taccgagctg      120 cagaccacca tccacgacat catcctggag tgtgtgtact gtaagcagca gctgctgagg      180
agagaggtgt acgaccggga cctgtgtatc gtgtacaggg acggcaatcc ctacgccgtg      240
tgtgacaagt gcctgaagtt ctacagcaag atcagcgagt accggcacta ctgctacagc      300
ctgtacggca ccaccctgga gcagcagtac aacaagcccc tgtgtgacct gctgatccgg      360
tgtatcaact gccagaagcc cctgcagaga cacctggaca gaagcagcg gttccacaac      420 atcaggggca gatggaccgg cagatgtatg agctgctgcc ggagcagcag aaccagaagg      480
gagacccagc tgagaggccg aagagaaga agccacggcg ataccccac cctgcacgag      540 tacatgctgg acctgcagcc tgagaccacc gatctgtacg gctacggcca gctgaatgac      600
agcagcgagg aggaggatga gatcgacggc cctgccggcc aggccgagcc cgacagagcc      660
cactacaaca tcgtgacctt tgctgtaag tgtgacagca ccctgagact gtgcgtgcag      720
agcacccacg tggacatcag aaccctggag gatctgctga tgggcaccct gggcatcgtg      780
tgtcccatct gctcccagaa acctgatga gcggccgc                              818

<210> SEQ ID NO 22
<211> LENGTH: 264
<212> TYPE: PRT
<213> ORGANISM: Artificial Sequence
<220> FEATURE:
<223> OTHER INFORMATION: HPV genotype 16 E6-E7 protein sequence
```

<400> SEQUENCE: 22

Met Asp Trp Thr Trp Ile Leu Phe Leu Val Ala Ala Ala Thr Arg Val
1               5                   10                  15

His Ser Phe Gln Asp Pro Gln Glu Ser Gly Arg Lys Leu Pro Gln Leu
            20                  25                  30

Cys Thr Glu Leu Gln Thr Thr Ile His Asp Ile Ile Leu Glu Cys Val
        35                  40                  45

Tyr Cys Lys Gln Gln Leu Leu Arg Arg Glu Val Tyr Asp Arg Asp Leu
    50                  55                  60

Cys Ile Val Tyr Arg Asp Gly Asn Pro Tyr Ala Val Cys Asp Lys Cys
65                  70                  75                  80

Leu Lys Phe Tyr Ser Lys Ile Ser Glu Tyr Arg His Tyr Cys Tyr Ser
                85                  90                  95

Leu Tyr Gly Thr Thr Leu Glu Gln Gln Tyr Asn Lys Pro Leu Cys Asp
            100                 105                 110

Leu Leu Ile Arg Cys Ile Asn Cys Gln Lys Pro Leu Gln Arg His Leu
        115                 120                 125

Asp Lys Lys Gln Arg Phe His Asn Ile Arg Gly Arg Trp Thr Gly Arg
    130                 135                 140

Cys Met Ser Cys Cys Arg Ser Ser Arg Thr Arg Arg Glu Thr Gln Leu
145                 150                 155                 160

Arg Gly Arg Lys Arg Arg Ser His Gly Asp Thr Pro Thr Leu His Glu
                165                 170                 175

Tyr Met Leu Asp Leu Gln Pro Glu Thr Thr Asp Leu Tyr Gly Tyr Gly
            180                 185                 190

Gln Leu Asn Asp Ser Ser Glu Glu Glu Asp Glu Ile Asp Gly Pro Ala
        195                 200                 205

Gly Gln Ala Glu Pro Asp Arg Ala His Tyr Asn Ile Val Thr Phe Cys
    210                 215                 220

Cys Lys Cys Asp Ser Thr Leu Arg Leu Cys Val Gln Ser Thr His Val
225                 230                 235                 240

Asp Ile Arg Thr Leu Glu Asp Leu Leu Met Gly Thr Leu Gly Ile Val
                245                 250                 255

Cys Pro Ile Cys Ser Gln Lys Pro
            260

<210> SEQ ID NO 23
<211> LENGTH: 837
<212> TYPE: DNA
<213> ORGANISM: Artificial Sequence
<220> FEATURE:
<223> OTHER INFORMATION: HPV genotype 18 E6-E7 DNA sequence

<400> SEQUENCE: 23
atggactgga cctggatcct gttcctggtg gccgctgcca cacgggtgca cagcgccaga      60
ttcgaggacc ccaccaggag cggctacaag ctgcccgatc tgtgtaccga gctgaacacc     120
agcctgcagg acatcgagat cacctgtgtg tactgtaaga ccgtgctgga gctgaccgag     180
gtgttcgaga aggaccctgtt cgtggtgtac agggacagca tccccacgc cgcctgccac     240 aagtgtatcg acttctacag ccggatccgg gagctgagac actacagcga cagcgtgtac     300
ggcgataccc tggagaagct gaccaacacc ggcctgtaca acctgctgat ccggtgcctg     360
agatgccaga agcccctgct gagacacctg aacgagaagc ggcggttcca caacatcgcc     420
ggccactaca gaggccagtg ccacagctgc tgtaacaggg ccaggcagga gagactgcag     480

```
cggagaagag agacccaggt gaggggcagg aagagaagaa gccacggccc caaggccacc    540
ctgcaggata tcgtgctgca cctggagccc cagaatgaga tccccgtgga tctgctgggc    600
cacggccagc tgtccgacag cgaggaggag aacgacgaga tcgacggcgt gaatcaccag    660
cacctgcctg ccagaagagc cgagcctcag aggcacacca tgctgtgtat gtgctgtaag    720
tgtgaggccc ggatcgaact ggtggtggag agcagcgccg acgacctgag agccttccag    780
cagctgttcc tgaacaccct gagcttcgtg tgtccttggt gtgccagcca gcagtga      837
```

<210> SEQ ID NO 24
<211> LENGTH: 278
<212> TYPE: PRT
<213> ORGANISM: Artificial Sequence
<220> FEATURE:
<223> OTHER INFORMATION: HPV genotype 18 E6-E7 protein sequence

<400> SEQUENCE: 24

```
Met Asp Trp Thr Trp Ile Leu Phe Leu Val Ala Ala Ala Thr Arg Val
1               5                   10                  15

His Ser Ala Arg Phe Glu Asp Pro Thr Arg Ser Gly Tyr Lys Leu Pro
            20                  25                  30

Asp Leu Cys Thr Glu Leu Asn Thr Ser Leu Gln Asp Ile Glu Ile Thr
        35                  40                  45

Cys Val Tyr Cys Lys Thr Val Leu Glu Leu Thr Glu Val Phe Glu Lys
    50                  55                  60

Asp Leu Phe Val Val Tyr Arg Asp Ser Ile Pro His Ala Ala Cys His
65                  70                  75                  80

Lys Cys Ile Asp Phe Tyr Ser Arg Ile Arg Glu Leu Arg His Tyr Ser
                85                  90                  95

Asp Ser Val Tyr Gly Asp Thr Leu Glu Lys Leu Thr Asn Thr Gly Leu
            100                 105                 110

Tyr Asn Leu Leu Ile Arg Cys Leu Arg Cys Gln Lys Pro Leu Leu Arg
        115                 120                 125

His Leu Asn Glu Lys Arg Arg Phe His Asn Ile Ala Gly His Tyr Arg
    130                 135                 140

Gly Gln Cys His Ser Cys Cys Asn Arg Ala Arg Gln Glu Arg Leu Gln
145                 150                 155                 160

Arg Arg Arg Glu Thr Gln Val Arg Gly Arg Lys Arg Arg Ser His Gly
                165                 170                 175

Pro Lys Ala Thr Leu Gln Asp Ile Val Leu His Leu Glu Pro Gln Asn
            180                 185                 190

Glu Ile Pro Val Asp Leu Leu Gly His Gly Gln Leu Ser Asp Ser Glu
        195                 200                 205

Glu Glu Asn Asp Glu Ile Asp Gly Val Asn His Gln His Leu Pro Ala
    210                 215                 220

Arg Arg Ala Glu Pro Gln Arg His Thr Met Leu Cys Met Cys Cys Lys
225                 230                 235                 240

Cys Glu Ala Arg Ile Glu Leu Val Val Glu Ser Ser Ala Asp Asp Leu
                245                 250                 255

Arg Ala Phe Gln Gln Leu Phe Leu Asn Thr Leu Ser Phe Val Cys Pro
            260                 265                 270

Trp Cys Ala Ser Gln Gln
            275
```

```
<210> SEQ ID NO 25
<211> LENGTH: 279
<212> TYPE: PRT
<213> ORGANISM: Artificial Sequence
<220> FEATURE:
<223> OTHER INFORMATION: HPV45 E6/E7 protein sequence

<400> SEQUENCE: 25

Met Asp Trp Thr Trp Ile Leu Phe Leu Val Ala Ala Ala Thr Arg Val
1               5                   10                  15

His Ser Ala Arg Phe Asp Asp Pro Lys Gln Ser Gly Tyr Lys Leu Pro
            20                  25                  30

Asp Leu Cys Thr Glu Leu Asn Thr Ser Leu Gln Asp Val Ser Ile Ala
        35                  40                  45

Cys Val Tyr Cys Lys Ala Thr Leu Glu Arg Thr Glu Val Tyr Gln Lys
    50                  55                  60

Asp Leu Cys Ile Val Tyr Arg Asp Cys Ile Ala Tyr Ala Ala Cys His
65                  70                  75                  80

Lys Cys Ile Asp Phe Tyr Ser Arg Ile Arg Glu Leu Arg Tyr Tyr Ser
                85                  90                  95

Asn Ser Val Tyr Gly Glu Thr Leu Glu Lys Ile Thr Asn Thr Glu Leu
            100                 105                 110

Tyr Asn Leu Leu Ile Arg Cys Leu Arg Cys Gln Lys Pro Leu Arg Arg
        115                 120                 125

His Leu Lys Asp Lys Arg Arg Phe His Ser Ile Ala Gly Gln Tyr Arg
    130                 135                 140

Gly Gln Cys Asn Thr Cys Cys Asp Gln Ala Arg Gln Glu Arg Leu Arg
145                 150                 155                 160

Arg Arg Arg Glu Thr Gln Val Arg Gly Arg Lys Arg Arg Ser His Gly
                165                 170                 175

Pro Arg Ala Thr Leu Gln Glu Ile Val Leu His Leu Glu Pro Gln Asn
            180                 185                 190

Glu Leu Asp Pro Val Asp Leu Leu Gly Tyr Gly Gln Leu Ser Glu Ser
        195                 200                 205

Glu Glu Glu Asn Asp Glu Ala Asp Gly Val Ser His Ala Gln Leu Pro
    210                 215                 220

Ala Arg Arg Ala Glu Pro Gln Arg His Lys Ile Leu Cys Val Cys Cys
225                 230                 235                 240

Lys Cys Asp Gly Arg Ile Glu Leu Thr Val Glu Ile Ser Ala Glu Asp
                245                 250                 255

Leu Arg Thr Leu Gln Gln Leu Phe Leu Ser Thr Leu Ser Phe Val Cys
            260                 265                 270

Pro Trp Cys Ala Thr Asn Gln
        275

<210> SEQ ID NO 26
<211> LENGTH: 282
<212> TYPE: PRT
<213> ORGANISM: Artificial Sequence
<220> FEATURE:
<223> OTHER INFORMATION: HPV39 E6/E7 protein sequence

<400> SEQUENCE: 26

Met Asp Trp Thr Trp Ile Leu Phe Leu Val Ala Ala Ala Thr Arg Val
1               5                   10                  15

His Ser Ala Arg Phe His Asn Pro Ala Glu Ser Gly Tyr Lys Leu Pro
            20                  25                  30
```

```
Asp Leu Cys Thr Thr Leu Asp Thr Thr Leu Gln Asp Ile Thr Ile Ala
            35                  40                  45

Cys Val Tyr Cys Arg Arg Pro Leu Gln Gln Thr Glu Val Tyr Glu Ser
        50                  55                  60

Asp Leu Tyr Val Val Tyr Arg Asp Gly Glu Pro Leu Ala Ala Cys Gln
65                      70                  75                  80

Ser Cys Ile Lys Phe Tyr Ala Lys Ile Arg Glu Leu Arg Tyr Tyr Ser
                85                  90                  95

Asp Ser Val Tyr Ala Thr Thr Leu Glu Asn Ile Thr Asn Thr Lys Leu
            100                 105                 110

Tyr Asn Leu Leu Ile Arg Cys Met Cys Cys Leu Lys Pro Leu Leu Arg
            115                 120                 125

His Leu Asn Ser Lys Arg Arg Phe His Lys Ile Ala Gly Ser Tyr Thr
            130                 135                 140

Gly Gln Cys Arg Arg Cys Trp Thr Thr Lys Arg Glu Asp Arg Arg Leu
145                     150                 155                 160

Thr Arg Arg Glu Thr Gln Val Arg Gly Arg Lys Arg Arg Ser Arg Gly
                165                 170                 175

Pro Lys Pro Thr Leu Gln Glu Ile Val Leu Asp Leu Cys Pro Tyr Asn
            180                 185                 190

Glu Ile Gln Pro Val Asp Leu Val Gly His Gly Gln Leu Gly Glu Ser
            195                 200                 205

Glu Asp Glu Ile Asp Glu Pro Asp His Ala Val Asn His Gln His Gln
            210                 215                 220

Leu Leu Ala Arg Arg Asp Glu Pro Gln Arg His Thr Ile Gln Cys Ser
225                     230                 235                 240

Cys Cys Lys Cys Asn Asn Thr Leu Gln Leu Val Val Glu Ala Ser Arg
                245                 250                 255

Asp Thr Leu Arg Gln Leu Gln Gln Leu Phe Met Asp Ser Leu Gly Phe
            260                 265                 270

Val Cys Pro Trp Cys Ala Thr Ala Asn Gln
            275                 280
```